(12) United States Patent
Ashman et al.

(10) Patent No.: US 7,879,812 B2
(45) Date of Patent: Feb. 1, 2011

(54) IMMUNOMODULATORY OLIGONUCLEOTIDES AND METHODS OF USE THEREFOR

(75) Inventors: Robert Ashman, Iowa City, IA (US); Petar Lenert, Iowa City, IA (US)

(73) Assignee: University of Iowa Research Foundation, Iowa City, IA (US)

( * ) Notice: Subject to any disclaimer, the term of this patent is extended or adjusted under 35 U.S.C. 154(b) by 158 days.

(21) Appl. No.: 12/185,418

(22) Filed: Aug. 4, 2008

(65) Prior Publication Data

US 2010/0081706 A1    Apr. 1, 2010

Related U.S. Application Data

(60) Provisional application No. 60/954,193, filed on Aug. 6, 2007.

(51) Int. Cl.
*A01N 43/04*     (2006.01)
*C12Q 1/68*      (2006.01)
*C12P 19/34*     (2006.01)
*C12N 15/63*     (2006.01)
*C07H 21/02*     (2006.01)

(52) U.S. Cl. .......................... 514/44; 435/6; 435/91.1; 435/455; 536/23.1

(58) Field of Classification Search ............... 435/6, 435/91.1, 91.31, 455; 536/23.1, 24.3, 24.5; 514/44
See application file for complete search history.

(56) References Cited

U.S. PATENT DOCUMENTS

| | | | |
|---|---|---|---|
| 6,194,388 B1 | 2/2001 | Krieg et al. | 514/44 |
| 6,207,646 B1 | 3/2001 | Krieg et al. | 514/44 |
| 6,218,371 B1 | 4/2001 | Krieg et al. | 514/44 |
| 6,239,116 B1 | 5/2001 | Krieg et al. | 514/44 |
| 6,339,068 B1 | 1/2002 | Krieg et al. | 514/44 |
| 6,406,705 B1 | 6/2002 | Davis et al. | 424/278.1 |
| 6,429,199 B1 | 8/2002 | Krieg et al. | 514/44 |
| 2005/0239733 A1 | 10/2005 | Jurk et al. | 514/44 |

FOREIGN PATENT DOCUMENTS

WO   WO 00/14217   3/2000
WO   WO 03/086280  10/2003

OTHER PUBLICATIONS

Crooke, S., Ann. Rev. Medicine, vol. 55, pp. 61-95 (2004).*
Peracchi et al., Rev. Med. Virol., vol. 14, pp. 47-64 (2004).*
Agrawal et al., Molecular Med. Today, vol. 6, pp. 72-81 (2000).*
Chirila et al., Biomaterials, vol. 23, pp. 321-342 (2002).*
Opalinska et al., Nature Rev., vol. 1, pp. 503-514 (2002).*
Ashman et al., "Sequence requirements for oligodeoxyribonucleotide inhibitory activity," *International Immunology*, 17(4):411-420, 2005.
Bauer et al., "Human TLR9 confers responsiveness to bacterial DNA via species-specific CpG motif recognition," *Proc. Natl. Acad. Sci. USA*, 98:9237-9242, 2001.
Heil et al.,"The Toll-like receptor 7 (TLR7)-specific stimulus loxoribine uncovers a strong relationship within the TLR7, 8 and 9 subfamily," *Eur. J. Immunol.*, 33:2987-2997, 2003.
Hemmi et al.,"A Toll-like receptor recognizes bacterial DNA," *Nature*, 408:740-745, 2000.
Lenert et al., "CpG stimulation of primary mouse B cells is blocked by inhibitory oligodeoxyribonucleotides at a site proximal to NF-kappaB activation," *Antisense Nucleic Acid Drug Dev.*, 11:247-256, 2001.
Lenert et al., "Extended sequence preferences for oligodeoxyribonucleotide activity," *Immunology*, 117:474-481, 2006.
Lenert et al., "Inhibitory oligonucleotides block the induction of AP-1 transcription factor by stimulatory CpG oligonucleotides in B cells," *Antisense Nucleic Acid Drug Dev.*, 13:143-150, 2003.
Stunz et al., "Inhibitory oligonucleotides specifically block effects of stimulatory CpG oligonucleotides in B cells," *Eur. J. Immunol.*, 32:1212-1222, 2002.
Yamada et al., "Effect of suppressive DNA on CpG-induced immune activation," *J. Immunol.*, 169:5590-5594, 2002.
Zeuner et al., "Reduction of CpG-induced arthritis by suppressive oligodeoxynucleotides," *Arthritis Rheum.*, 46:2219-2224, 2002.

* cited by examiner

*Primary Examiner*—Jane Zara
(74) *Attorney, Agent, or Firm*—Fulbright & Jaworski

(57) ABSTRACT

The present invention is drawn a new class of oligodeoxynucleotides (ODNs) that inhibit ODN-activation of Toll-like receptor (TLR)9. Particular 4-5 base extensions at the 5' and of the previously described core inhibitory ODN sequence enhances their inhibitory activity against human cells expressing human TLR9. Methods of use also are provided.

37 Claims, No Drawings

SEQUENCE LISTING

```
<160> NUMBER OF SEQ ID NOS: 38

<210> SEQ ID NO 1
<211> LENGTH: 15
<212> TYPE: DNA
<213> ORGANISM: Artificial
<220> FEATURE:
<223> OTHER INFORMATION: Synthetic Primer

<400> SEQUENCE: 1
tatcctggag gggaa                                                          15

<210> SEQ ID NO 2
<211> LENGTH: 20
<212> TYPE: DNA
<213> ORGANISM: Artificial
<220> FEATURE:
<223> OTHER INFORMATION: Synthetic Primer

<400> SEQUENCE: 2
tcctttcctg gaggggaagt                                                     20

<210> SEQ ID NO 3
<211> LENGTH: 25
<212> TYPE: DNA
<213> ORGANISM: Artificial
<220> FEATURE:
<223> OTHER INFORMATION: Synthetic Primer

<400> SEQUENCE: 3
```

```
tcctatccta tcctggaggg gaagt                                          25

<210> SEQ ID NO 4
<211> LENGTH: 20
<212> TYPE: DNA
<213> ORGANISM: Artificial
<220> FEATURE:
<223> OTHER INFORMATION: Synthetic Primer

<400> SEQUENCE: 4
tcgtatcctg gagggggaagt                                               20

<210> SEQ ID NO 5
<211> LENGTH: 20
<212> TYPE: DNA
<213> ORGANISM: Artificial
<220> FEATURE:
<223> OTHER INFORMATION: Synthetic Primer

<400> SEQUENCE: 5
taatatcctg gaggggaagt                                                20

<210> SEQ ID NO 6
<211> LENGTH: 19
<212> TYPE: DNA
<213> ORGANISM: Artificial
<220> FEATURE:
<223> OTHER INFORMATION: Synthetic Primer

<400> SEQUENCE: 6
cctatcctgg aggggaagt                                                 19

<210> SEQ ID NO 7
<211> LENGTH: 20
<212> TYPE: DNA
<213> ORGANISM: Artificial
<220> FEATURE:
<223> OTHER INFORMATION: Synthetic Primer

<400> SEQUENCE: 7
tcctatcctg gaggggaagt                                                20

<210> SEQ ID NO 8
<211> LENGTH: 26
<212> TYPE: DNA
<213> ORGANISM: Artificial
<220> FEATURE:
<223> OTHER INFORMATION: Synthetic primer
<220> FEATURE:
<221> NAME/KEY: misc_feature
<222> LOCATION: (4)..(6)
<223> OTHER INFORMATION: n is a, c, g, or t
<220> FEATURE:
<221> NAME/KEY: misc_feature
<222> LOCATION: (11)..(16)
<223> OTHER INFORMATION: n is a, c, g, or t
<220> FEATURE:
<221> NAME/KEY: misc_feature
<222> LOCATION: (21)..(23)
<223> OTHER INFORMATION: n is a, c, g, or t

<400> SEQUENCE: 8
cctnnngggy nnnnnnyccc nnnagg                                         26

<210> SEQ ID NO 9
<211> LENGTH: 30
<212> TYPE: DNA
```

```
<213> ORGANISM: Artificial
<220> FEATURE:
<223> OTHER INFORMATION: Synthetic primer

<400> SEQUENCE: 9
tatcctggag gggaattccc ctccaggata                                          30

<210> SEQ ID NO 10
<211> LENGTH: 13
<212> TYPE: DNA
<213> ORGANISM: Artificial
<220> FEATURE:
<223> OTHER INFORMATION: Synthetic primer
<220> FEATURE:
<221> NAME/KEY: misc_feature
<222> LOCATION: (4)..(7)
<223> OTHER INFORMATION: n is a, c, g, or t
<220> FEATURE:
<221> NAME/KEY: misc_feature
<222> LOCATION: (12)..(13)
<223> OTHER INFORMATION: n is a, c, g, or t

<400> SEQUENCE: 10
cctnnnnggg gnn                                                            13

<210> SEQ ID NO 11
<211> LENGTH: 15
<212> TYPE: DNA
<213> ORGANISM: Homo sapiens

<400> SEQUENCE: 11
tcctggcggg gaagt                                                          15

<210> SEQ ID NO 12
<211> LENGTH: 15
<212> TYPE: DNA
<213> ORGANISM: Homo sapiens

<400> SEQUENCE: 12
tactggaggg gaagt                                                          15

<210> SEQ ID NO 13
<211> LENGTH: 15
<212> TYPE: DNA
<213> ORGANISM: Homo sapiens

<400> SEQUENCE: 13
tcatggaggg gaagt                                                          15

<210> SEQ ID NO 14
<211> LENGTH: 15
<212> TYPE: DNA
<213> ORGANISM: Homo sapiens

<400> SEQUENCE: 14
taatggaggg gaagt                                                          15

<210> SEQ ID NO 15
<211> LENGTH: 15
<212> TYPE: DNA
<213> ORGANISM: Homo sapiens

<400> SEQUENCE: 15
tcctgcaggg gaagt                                                          15
```

```
<210> SEQ ID NO 16
<211> LENGTH: 15
<212> TYPE: DNA
<213> ORGANISM: Homo sapiens

<400> SEQUENCE: 16
tcctccaggg gaagt                                                    15

<210> SEQ ID NO 17
<211> LENGTH: 15
<212> TYPE: DNA
<213> ORGANISM: Homo sapiens

<400> SEQUENCE: 17
tcctggagtg gaagt                                                    15

<210> SEQ ID NO 18
<211> LENGTH: 15
<212> TYPE: DNA
<213> ORGANISM: Homo sapiens

<400> SEQUENCE: 18
tcctggaggt gaagt                                                    15

<210> SEQ ID NO 19
<211> LENGTH: 15
<212> TYPE: DNA
<213> ORGANISM: Homo sapiens

<400> SEQUENCE: 19
tcctggagcg gaagt                                                    15

<210> SEQ ID NO 20
<211> LENGTH: 15
<212> TYPE: DNA
<213> ORGANISM: Homo sapiens

<400> SEQUENCE: 20
tcctggaggc gaagt                                                    15

<210> SEQ ID NO 21
<211> LENGTH: 15
<212> TYPE: DNA
<213> ORGANISM: Homo sapiens

<400> SEQUENCE: 21
tcctggacgg caagt                                                    15

<210> SEQ ID NO 22
<211> LENGTH: 11
<212> TYPE: DNA
<213> ORGANISM: Homo sapiens

<400> SEQUENCE: 22
tcctggaggg g                                                        11

<210> SEQ ID NO 23
<211> LENGTH: 14
<212> TYPE: DNA
<213> ORGANISM: Homo sapiens

<400> SEQUENCE: 23
cctggagggg aagt                                                     14
```

```
<210> SEQ ID NO 24
<211> LENGTH: 10
<212> TYPE: DNA
<213> ORGANISM: Homo sapiens

<400> SEQUENCE: 24
cctggagggg                                                              10

<210> SEQ ID NO 25
<211> LENGTH: 13
<212> TYPE: DNA
<213> ORGANISM: Homo sapiens

<400> SEQUENCE: 25
ctggagggga agt                                                          13

<210> SEQ ID NO 26
<211> LENGTH: 14
<212> TYPE: DNA
<213> ORGANISM: Homo sapiens

<400> SEQUENCE: 26
ccaggagggg aagt                                                         14

<210> SEQ ID NO 27
<211> LENGTH: 19
<212> TYPE: DNA
<213> ORGANISM: Homo sapiens

<400> SEQUENCE: 27
tccttcctgg aggggaagt                                                    19

<210> SEQ ID NO 28
<211> LENGTH: 19
<212> TYPE: DNA
<213> ORGANISM: Homo sapiens

<400> SEQUENCE: 28
tcctatcctg gaggggaag                                                    19

<210> SEQ ID NO 29
<211> LENGTH: 19
<212> TYPE: DNA
<213> ORGANISM: Homo sapiens

<400> SEQUENCE: 29
tcctatcctg gaggggaag                                                    19

<210> SEQ ID NO 30
<211> LENGTH: 19
<212> TYPE: DNA
<213> ORGANISM: Homo sapiens

<400> SEQUENCE: 30
tcgtatcctg gaggggaag                                                    19

<210> SEQ ID NO 31
<211> LENGTH: 19
<212> TYPE: DNA
<213> ORGANISM: Homo sapiens

<400> SEQUENCE: 31
taatatcctg gaggggaag                                                    19
```

```
<210> SEQ ID NO 32
<211> LENGTH: 18
<212> TYPE: DNA
<213> ORGANISM: Homo sapiens

<400> SEQUENCE: 32
cctatcctgg aggggaag                                                 18

<210> SEQ ID NO 33
<211> LENGTH: 19
<212> TYPE: DNA
<213> ORGANISM: Homo sapiens

<400> SEQUENCE: 33
tcctataatg gagggaag                                                 19

<210> SEQ ID NO 34
<211> LENGTH: 16
<212> TYPE: DNA
<213> ORGANISM: Homo sapiens

<400> SEQUENCE: 34
cctcaagctt gagggg                                                   16

<210> SEQ ID NO 35
<211> LENGTH: 16
<212> TYPE: DNA
<213> ORGANISM: Homo sapiens

<400> SEQUENCE: 35
cctcaagggt gagggg                                                   16

<210> SEQ ID NO 36
<211> LENGTH: 20
<212> TYPE: DNA
<213> ORGANISM: Homo sapiens

<400> SEQUENCE: 36
gagcaagctg gaccttccat                                               20

<210> SEQ ID NO 37
<211> LENGTH: 20
<212> TYPE: DNA
<213> ORGANISM: Homo sapiens

<400> SEQUENCE: 37
gaccaagcgg gaccttccat                                               20

<210> SEQ ID NO 38
<211> LENGTH: 18
<212> TYPE: DNA
<213> ORGANISM: Homo sapiens

<400> SEQUENCE: 38
ttagggttag ggttaggg                                                 18
```

IMMUNOMODULATORY OLIGONUCLEOTIDES AND METHODS OF USE THEREFOR

The present application claims benefit of U.S. Provisional Application Ser. No. 60/954,193, filed Aug. 6, 2007, the entire contents of which are hereby incorporated by reference.

This invention was made with government support under grant no. AI 047374 awarded by the National Institutes of Health. The government has certain rights in the invention.

BACKGROUND OF THE INVENTION

I. Field of the Invention

The present invention relates to the fields of cell biology, immunology and pathology. More specifically, the invention deals with optimized sequences of oligodeoxynucleotides (ODNs) that modulate immune responses, in particular, those involving Toll-like receptors (TLRs).

II. Related Art

Reaction to certain motifs in bacterial DNA is an important function of natural immunity. Bacterial DNA has long been known to be mitogenic for mammalian B lymphocytes (B cells), whereas mammalian DNA generally is not. The discovery that this immune recognition was directed to specific DNA sequences centered on a motif containing an unmethylated CpG dinucleotide opened the field to molecular immunologic approaches (Krieg et al., 1995). The immunostimulatory effects of so-called CpG DNA can be reproduced using synthetic oligodeoxynucleotides (ODN) containing CpG dinucleotides in the context of certain preferred flanking sequence, a CpG motif. CpG-containing ODN (CpG-ODN) have been reported to exert a number of effects on various types of cells of the immune system, including protecting primary B cells from apoptosis, promotion of cell cycle entry, and skewing an immune response toward a Th1-type immune response, e.g., induction of interleukin 6 (IL-6), interleukin 12 (IL-12), γ interferon (IFN-γ), activation of antigen-specific cytolytic T lymphocytes (CTL), and induction in the mouse of IgG2a.

It has been reported that the immunomodulatory effects of CpG DNA involve signaling by Toll-like receptor 9 (TLR9). It is believed that CpG DNA is internalized into a cell via a sequence-nonspecific pathway and traffics to the endosomal compartment, where it interacts with TLR9 in a sequence-specific manner. TLR9 signaling pathways lead to induction of a number of immune-function related genes, including notably NF-κB, among others.

The TLRs are a large family of receptors that recognize specific molecular structures that are present in pathogens (pathogen-associated molecular patterns or PAMPs) and are also termed pattern recognition receptors (PRRs). Immune cells expressing PRRs are activated upon recognition of PAMPs and trigger the generation of optimal adaptive immune responses. PRRs consisting of 10 different TLR subtypes, TLR1 to TLR10, have been described. Such TLRs have been described to be involved in the recognition of double-stranded RNA (TLR3), lipopolysaccharide (LPS) (TLR4), bacterial flagellin (TLR5), small anti-viral compounds (TLR7 and TLR8), and bacterial DNA or CpG ODN (TLR9). Reviewed in Uhlmann et al. (2003). In addition, RNA molecules were recently identified that are believed to interact with and signal through TLR7 and TLR8 (PCT/US03/10406). Such immunostimulatory RNA molecules are believed to have a base sequence that includes at least one guanine and at least one uracil. The immunostimulatory G,U-rich RNA does not require a CpG motif as described for TLR9. The corresponding class of RNA molecules found in nature is believed to be present in ribosomal RNA (rRNA), transfer RNA (tRNA), messenger RNA (mRNA), and viral RNA (vRNA).

Following the discovery of immunostimulatory CpG DNA, a number of reports appeared describing short DNA sequences with TLR-restricted immunoinhibitory effects. It has long been known that poly-G sequences were immunoinhibitory. PCT application WO 00/14217 describes ODN containing an inhibitory motif $N_1N_2GN_3G$ in which at least any two of $N_1$, $N_2$, and $N_3$ are G (guanosine). Dr. Ashman's laboratory described a group of inhibitory 15-mer ODN, having three or four consecutive Gs, that blocked apoptosis protection and cell-cycle entry induced by stimulatory ODN (Lenert et al., 2001; Stunz et al., 2002; Lenert et al., 2003). The immunoinhibitory effect of these ODN was reported to be specific for CpG-ODN and to involve a mechanism other than simple competition for cellular uptake (Stunz et al., 2002). Independently, Klinman and colleagues reported a single immunoinhibitory ODN (Zeuner et al., 2002; Yamada et al., 2002).

SUMMARY OF THE INVENTION

Thus, in accordance with the present invention, there is provided an oligonucleotide of no more than about 50 bases comprising the sequence 5'-X-$Y_1Y_2$-TATCCTGGAGGG-GAA-$Y_3Y_4$-3' (SEQ ID NO:1), wherein X is T or null, and $Y_1$ and $Y_2$ are independently A, G, C or T, $Y_3$ and $Y_4$ are independently A, G, C, T or null, but excluding TCCTATCCTG-GAGGGGAAG (SEQ ID NO:7). $Y_1$ and $Y_2$ may be the same or different. Independently, one of $Y_1$ and $Y_2$ may be C, one of $Y_1$ and $Y_2$ may be G, and/or one of $Y_1$ and $Y_2$ may be A. In one embodiment, $Y_3$ may be G and $Y_4$ may be T. The oligonucleotide may consist of 50 bases, 49 bases, 48 bases, 47 bases, 46 bases, 45 bases, 44 bases, 43 bases, 42 bases, 41 bases, 40 bases, 39 bases, 38 bases, 37 bases, 36 bases, 35 bases, 34 bases, 33 bases, 32 bases, 31 bases, 30 bases, 29 bases, 28 bases, 27 bases, 26 bases, 25 bases, 24 bases, 23 bases, 22 bases, 21 bases, 20 bases, 19 bases, 18 bases, or 17 bases. The oligonucleotide may have a phosphodiester, phosphorothioate, phosphoroamidate, or phorphorodithioate backbone. The oligonucleotide may be dispersed in a pharmaceutically acceptable buffer, diluent or excipient.

Also provided is a method of inhibiting a Toll-like receptor (TLR) signaling comprising contacting a cell expressing with a TLR an oligonucleotide of no more than about 50 bases dispersed in a pharmaceutically acceptable buffer, diluent or excipient, said oligonucleotide comprising the sequence 5'-X-$Y_1Y_2$-TATCCTGGAGGGGAA-$Y_3Y_4$-3' (SEQ ID NO:1), wherein X is T or null, and $Y_1$ and $Y_2$ are independently A, G, C or T, $Y_3$ and $Y_4$ are independently A, G, C, T or null, but excluding TCCTATCCTGGAGGGGAAG (SEQ ID NO:7). $Y_1$ and $Y_2$ may be the same or different. Independently, one of $Y_1$ and $Y_2$ may be C, one of $Y_1$ and $Y_2$ may be G, and/or one of $Y_1$ and $Y_2$ may be A. In one embodiment, $Y_3$ may be G and $Y_4$ may be T. The oligonucleotide may consist of 50 bases, 49 bases, 48 bases, 47 bases, 46 bases, 45 bases, 44 bases, 43 bases, 42 bases, 41 bases, 40 bases, 39 bases, 38 bases, 37 bases, 36 bases, 35 bases, 34 bases, 33 bases, 32 bases, 31 bases, 30 bases, 29 bases, 28 bases, 27 bases, 26 bases, 25 bases, 24 bases, 23 bases, 22 bases, 21 bases, 20 bases, 19 bases, 18 bases, or 17 bases. The oligonucleotide may have a phosphodiester, phosphorothioate, phosphoroamidate, or phosphorodithioate backbone. The oligonucleotide may be encapsulated in a lipid delivery vehicle.

The cell may be located in an animal, such as a mouse or a human. The cell may be a B-cell, and the TLR may be TLR9. The human may suffer from or be at risk of an unwanted immune reaction, such as an autoimmune reaction, allergic reaction, a detrimental immune response to infection. The oligonucleotide may be administered orally, intravenously, intra-arterially, subcutaneously, intramuscularly, topically, by inhalation, intranasally, or intraocularly. The method may further comprise administering to said human an anti-inflammatory or immunosuppressive agent. The method may further comprise administering said oligonucleotide to said human at least a second time. The subject may have an infection that results or could result in septic shock.

In still a further embodiment, there is provided a palindromic oligonucleotide of 24 to about 50 bases comprising the sequence:

(SEQ ID NO: 8)
5'-CCTX$_1$X$_2$X$_3$GGGYX$_4$X$_5$Z$_n$X$_6$X$_7$Y'CCCX$_8$X$_9$X$_{10}$AGG-3' wherein $X_1$-$X_5$ are independently A, G, C or T, Y is G or null, Z is a spacer nucleotide segment of length n, wherein n is 0-10, Y' is C when Y is G, and Y' is null where Y is null, $X_6$ is selected so as to base pair with $X_5$, $X_7$ is selected so as to base pair with $X_4$, $X_8$ is selected so as to base pair with $X_3$, $X_9$ is selected so as to base pair with $X_2$, and $X_{10}$ is selected so as to base pair with $X_1$. The oligonucleotide may be 24-28 residues in length. The oligonucleotide may be completely palindromic or partially palindromic. The oligonucleotide may comprise a 3' mismatched sequence or a 5' mismatched sequence. The mismatched sequence may be 1-10 bases in length, or 1-5 bases in length. The oligonucleotide may have the sequence TATCCTGGAGGGGAATTCCCCTCCAGGATA (SEQ ID NO:9).

It is contemplated that any method or composition described herein can be implemented with respect to any other method or composition described herein.

The use of the word "a" or "an" when used in conjunction with the term "comprising" in the claims and/or the specification may mean "one," but it is also consistent with the meaning of "one or more," "at least one," and "one or more than one."

Other objects, features and advantages of the present invention will become apparent from the following detailed description. It should be understood, however, that the detailed description and the specific examples, while indicating specific embodiments of the invention, are given by way of illustration only, since various changes and modifications within the spirit and scope of the invention will become apparent to those skilled in the art from this detailed description.

DETAILED DESCRIPTION OF THE INVENTION

I. Definitions

As used herein, the term "antigen" refers to any biological molecule capable of eliciting specific immunity. Antigens specifically include peptides (oligopeptides, polypetides proteins, and glycosylated derivatives thereof), and polysaccharides. Peptide antigens can include preformed peptide antigens and polynucleotides encoding the peptide antigens.

As used herein, the term "autoimmune disease" refers to a disease caused by a breakdown of self-tolerance such that the adaptive immune system responds to self antigens and mediates cell and tissue damage. Autoimmune diseases specifically include, without limitation, insulin-dependent diabetes mellitus, inflammatory bowel disease, systemic lupus, rheumatoid arthritis, and multiple sclerosis. Additional specific examples of autoimmune diseases are provided below.

As used herein, the term "condition associated with CpG-mediated immunostimulation" refers to any disease or other condition in a subject in which there is immune activation associated with exposure of immune cells of the subject to CpG-containing material. Such conditions typically involve activation of TLR9 signaling in response to contact with the CpG.

As used herein, the term "conjugate" refers to any combination of two or more component parts that are linked together, directly or indirectly, via any physicochemical interaction. In one embodiment the conjugate is a combination of two or more component parts that are linked together, directly or indirectly, via covalent bonding.

As used herein, the term "cytidine derivative" refers to a cytidine-like nucleotide (excluding cytidine) having a chemical modification involving the cytosine base, cytidine nucleoside sugar, or both the cytosine base and the cytidine nucleoside sugar. Cytidine derivatives specifically include, without limitation, 5-methylcytidine, 2'-O-methylcytidine, 5-bromocytidine, 5-hydroxycytidine, ribocytidine, and ara-C (cytosine-β-D-arabinofuranoside). Additional specific cytidine derivatives are disclosed further below.

As used herein, the term "effective amount" refers to that amount of a substance that is sufficient to bring about a desired biologic effect. An effective amount can but need not be limited to an amount administered in a single administration.

As used herein, the term "guanosine derivative" refers to a guanosine-like nucleotide (excluding guanosine) having a chemical modification involving the guanine base, guanosine nucleoside sugar, or both the guanine base and the guanosine nucleoside sugar. Guanosine derivatives specifically include, without limitation, 7-deazaguanosine. Additional specific guanosine derivatives are disclosed further below.

As used herein, the term "immune cell that is sensitive to a CpG nucleic acid molecule" refers to a naturally-occurring or engineered cell that is activated in response to contact with a CpG nucleic acid molecule. The activation can be manifested in terms of an increase of gene transcription, cell-cycle entry, proliferation, resistance to apoptosis, secretion of a gene product, expression of a gene product, or cytolytic activity. In one embodiment the activation is manifested as an increase in TLR9 signaling.

As used herein, the term "immunoinhibitory nucleic acid molecule" refers to a nucleic acid molecule that is or that includes an inhibitory ODN of the invention.

As used herein, the term "immunostimulatory CpG nucleic acid molecule" refers to any CpG-containing nucleic acid molecule that is capable of activating an immune cell. At least the C of the CpG dinucleotide is typically, but not necessarily, unmethylated. Immunostimulatory CpG nucleic acid molecules are well described in a number of issued patents and published patent applications, including U.S. Pat. Nos. 6,194,388; 6,207,646; 6,218,371; 6,239,116; 6,339,068; 6,406,705; and 6,429,199.

As used herein, the term "immunostimulatory effect of a CpG nucleic acid molecule" refers to any activating or proliferative effect on an immune cell or population of immune cells that is associated with exposure of the immune cell or population of immune cells with a CpG nucleic acid molecule. An activating effect includes increased or de novo expression or secretion of a gene product compared to expression or secretion of that gene product by an immune cell or population of immune cells that has not been exposed to a CpG nucleic acid molecule.

As used herein, the term "infection with a CpG-containing microbe" refers to an abnormal presence of a nucleic acid-containing infectious agent in a host. An infection with a CpG-containing microbe specifically includes a bacterial, viral, fungal, or parasitic infection, and any combination thereof.

As used herein, the term "inflammation" refers to an antigen-nonspecific reaction of the innate immune system that involves accumulation and activation of leukocytes and plasma proteins at a site of infection, toxin exposure, or cell injury. Cytokines that are characteristic of inflammation include tumor necrosis factor α (TNF-α), interleukin 1 (IL-1), IL-6, IL-12, interferon α (IFN-α), interferon β (IFN-β), and chemokines.

As used herein, the term "inhibit" shall mean reduce an outcome or effect compared to normal.

As used herein, the term "inhibiting" refers to reducing an outcome or effect compared to normal.

As used herein, the term "isolated" as used to describe a compound shall mean removed from the natural environment in which the compound occurs in nature. In one embodiment isolated means removed from non-nucleic acid molecules of a cell.

As used herein, the term "pharmaceutically acceptable carrier" refers to one or more compatible solid or liquid filler, diluents or encapsulating substances which are suitable for administration to a human or other vertebrate animal.

As used herein, the term "phosphorothioate backbone" refers to a stabilized sugar phosphate backbone of a nucleic acid molecule in which a non-bridging phosphate oxygen is replaced by sulfur at least one internucleotide linkage. In one embodiment a non-bridging phosphate oxygen is replaced by sulfur at each and every internucleotide linkage.

As used herein, the term "sepsis" refers to a well-recognized clinical syndrome associated with a host's systemic inflammatory response to microbial invasion. Sepsis is typically signaled by fever or hypothermia, tachycardia, and tachypnea, and in severe instances can progress to hypotension, organ dysfunction, and even death.

As used herein, the term "subject" refers to a human or non-human vertebrate. Non-human vertebrates include livestock animals, companion animals, and laboratory animals. Non-human subjects also specifically include non-human primates as well as rodents. Non-human subjects also specifically include, without limitation, chickens, horses, cows, pigs, goats, dogs, cats, guinea pigs, hamsters, mink, and rabbits.

As used herein, the term "subject at risk of developing" a condition refers to a subject with a known or suspected exposure to an agent known to cause or to be associated with the condition or a known or suspected predisposition to develop the condition (e.g., a genetic marker for or a family history of the condition).

As used herein, the term "Th1-like" refers to having a feature characteristic of a Th1 immune response. A Th1 immune response characteristically may include induction of certain cytokines such as IFN-γ, secretion (in mice) of IgG2a immunoglobulins, and macrophage activation. The term "Th1-like" is to be contrasted with the term "Th2-like," which refers to having a feature characteristic of a Th2 immune response. A Th2 immune response characteristically may include induction of certain cytokines such as IL-4 and IL-5, and (in mice) secretion of IgG1 and IgE.

As used herein, the term "TLR signaling" refers to any aspect of intracellular signaling associated with signaling through a TLR.

As used herein, the term "TLR7 signaling agonist" refers to any agent that is capable of inducing an increase in TLR7 signaling. TLR7 signaling agonists specifically include, without limitation, imiquimod (R-837; 1-(2-methylpropyl)-1H-imidazo[4,5-c]quinoline-4-amine), resiquimod (R-848; 4-amino-α,α-dimethyl-2-ethoxymethyl-1H-imi-dazo[4,5-c] quinoline-1-ethanol), mixtures of ribonucleosides consisting essentially of G and U, or isolated guanosine ribonucleotides such as loxoribine (7-allyl-7,8-dihydro-8-oxo-guanosine; Heil et al. (2003) and RNA or RNA-like molecules (PCT/US03/10406).

As used herein, the term "TLR8 signaling agonist" refers to any agent that is capable of inducing an increase in TLR8 signaling. TLR8 signaling agonists specifically include, without limitation, R-837 or R-848 (WO 02/22125), mixtures of ribonucleosides consisting essentially of G and U, and RNA or RNA-like molecules (PCT/US03/10406).

As used herein, the term "TLR9 signaling agonist" refers to any agent that is capable of inducing an increase in TLR9 signaling. TLR9 signaling agonists specifically include, without limitation, immunostimulatory CpG nucleic acid molecules.

As used herein, the term "treat" as used in reference to a disease or condition shall mean to intervene in such disease or condition so as to prevent or slow the development of, prevent or slow the progression of, halt the progression of, or eliminate the disease or condition.

II. Toll-Like Receptors

Toll-like receptors (TLRs) are a family of highly conserved polypeptides that play a critical role in innate immunity in mammals. Currently ten family members, designated TLR1-TLR10, have been identified. The cytoplasmic domains of the various TLRs are characterized by a Toll-interleukin 1 (IL-1) receptor (TIR) domain (Medzhitov et al., 1998). Recognition of microbial invasion by TLRs triggers activation of a signaling cascade that is evolutionarily conserved in *Drosophila* and mammals. The TIR domain-containing adapter protein MyD88 has been reported to associate with TLRs and to recruit IL-1 receptor-associated kinase (IRAK) and tumor necrosis factor (TNF) receptor-associated factor 6 (TRAF6) to the TLRs. The MyD88-dependent signaling pathway is believed to lead to activation of NF-κB transcription factors and c-Jun $NH_2$ terminal kinase (Jnk) mitogen-activated protein kinases (MAPKs), critical steps in immune activation and production of inflammatory cytokines. For a review, see Aderem et al. (2000).

While a number of specific TLR ligands have been reported, ligands for some TLRs remain to be identified. Ligands for TLR2 include peptidoglycan and lipopeptides (Yoshimura et al., 1999; Aliprantis et al., 1999). Viral-derived double-stranded RNA (dsRNA) and poly I:C, a synthetic analog of dsRNA, have been reported to be ligands of TLR3 (Alexopoulou et al., 2001). Lipopolysaccharide (LPS) is a ligand for TLR4 (Poltorak et al., 1998; Hoshino et al., 1999). Bacterial flagellin is a ligand for TLR5 (Hayashi et al., 2001). Peptidoglycan has been reported to be a ligand not only for TLR2 but also for TLR6 (Ozinsky et al., 2000; Takeuchi et al., 2001). Certain low molecular weight synthetic compounds, the imidazoquinolones imiquimod (R-837) and resiquimod (R-848), were reported to be ligands of TLR7 and TLR8 (Hemmi et al., 2002; Jurk et al., 2002). Bacterial DNA (CpG DNA) has been reported to be a TLR9 ligand (Hemmi et al., 2000; Bauer et al., 2001). RNA molecules were recently identified that are believed to interact with and signal through TLR7 and TLR8 (PCT/US03/10406).

In addition to having diverse ligands, the various TLRs are believed to be differentially expressed in various tissues and on various types of immune cells. For example, human TLR7 has been reported to be expressed in placenta, lung, spleen, lymph nodes, tonsil and on plasmacytoid precursor dendritic cells (pDCs) (Chuang et al., 2000; Kadowaki et al., 2001). Human TLR8 has been reported to be expressed in lung, peripheral blood leukocytes (PBL), placenta, spleen, lymph nodes, and on monocytes (Kadowaki et al., 2001; Chuang et al., 2000). Human TLR9 is reportedly expressed in spleen, lymph nodes, bone marrow, PBL, and on pDCs, and B cells (Kadowaki et al., 2001; Bauer et al., 2001; Chuang et al., 2000).

A. TLR7

Nucleotide and amino acid sequences of human and murine TLR7 are known. See, for example, GenBank Accession Nos. AF240467, AF245702, NM_016562, AF334942, NM_133211; and AAF60188, AAF78035, NP_057646, AAL73191, and AAL73192, the contents of all of which are incorporated herein by reference. Human TLR7 is reported to be 1049 amino acids long. Murine TLR7 is reported to be 1050 amino acids long. TLR7 polypeptides include an extracellular domain having a leucine-rich repeat region, a transmembrane domain, and an intracellular domain that includes a TIR domain.

B. TLR8

Nucleotide and amino acid sequences of human and murine TLR8 are known. See, for example, GenBank Accession Nos. AF246971, AF245703, NM_016610, XM_045706, AY_035890, NM.sub_133212; and AAF64061, AAF78036, NP_057694, XP_045706, AAK62677, and NP_573475, the contents of all of which is incorporated herein by reference. Human TLR8 is reported to exist in at least two isoforms, one 1041 amino acids long and the other 1059 amino acids long. Murine TLR8 is 1032 amino acids long. TLR8 polypeptides include an extracellular domain having a leucine-rich repeat region, a transmembrane domain, and an intracellular domain that includes a TIR domain.

C. TLR9

Nucleotide and amino acid sequences of human and murine TLR9 are known. See, for example, GenBank Accession Nos. NM_017442, AF259262, AB045180, AF245704, AB045181, AF348140, AF314224, NM_031178; and NP_059138, AAF72189, BAB19259, AAF78037, BAB19260, AAK29625, AAK28488, and NP_112455, the contents of all of which are incorporated herein by reference. Human TLR9 is reported to exist in at least two isoforms, one 1032 amino acids long and the other 1055 amino acids. Murine TLR9 is 1032 amino acids long. TLR9 polypeptides include an extracellular domain having a leucine-rich repeat region, a transmembrane domain, and an intracellular domain that includes a TIR domain.

III. Inhibitory ODNs

The invention provides inhibitory ODNs characterized at least in part by a TLR9-antagonist motif. Thus, in one aspect the invention provides a composition including an isolated immunoinhibitory nucleic acid molecule including a sequence:

5'-X-Y$_1$Y$_2$-TATCCTGGAGGGGAAGT-3' (SEQ ID NO: 1)

wherein X is T or null, and Y$_1$ and Y$_2$ are independently A, G, C or T. It will be appreciated that the inhibitory ODN according to this aspect of the invention includes an oligonucleotide of no more than about 50 bases, optionally no more than about 49, 48, 47, 46, 45, 44, 43, 42, 41, 40, 39, 38, 37, 36, 35, 34, 33, 32, 31, 30, 29, 28, 27, 26, 25, 24, 23, 22, 21, or 20 bases comprising the sequence. Also contemplated are ranges of size from 20-50 bases, 25-50, 30-50, 35-50 based, 40-50 bases, and 45-50 bases. Particular examples of ODNs include:

| | |
|---|---|
| TCCTTTCCTGGAGGGGAAGT | (SEQ ID NO: 2) |
| TCCTATCCTATCCTGGAGGGGAAGT | (SEQ ID NO: 3) |
| TCGTATCCTGGAGGGGAAGT | (SEQ ID NO: 4) |
| TAATATCCTGGAGGGGAAGT | (SEQ ID NO: 5) |
| -CCTATCCTGGAGGGGAAGT | (SEQ ID NO: 6) |

The invention also specifically contemplates exclusion of TCCTATCCTGGAGGGGAAG (SEQ ID NO:7).

Palindromic ODNs have been developed to improve the ability to treat lupus and other systemic autoimmune diseases. This structure combines the optimal primary inhibitory ODN structure (CCTxxxxGGG(G)xx) (SEQ ID NO:10) that is extended with the complementary sequence, thus creating a palindrome. A particular size for the palindromic ODN is between 24-28 nucleotides, although it can be up to about 50 nucleotides. One may also include a non-palindromic segment that separates the two complementary sequences, which will form a loop upon hybridization of the palindromic sequences. The loop can be 1, 2, 3, 4, 5, 6, 7, 8, 9, 10 or more bases. These ODNs can be delivered intraperitoneally, subcutaneously and orally. The resulting palindromic ODN was superior in blocking autoreactive B cell activation and anti-dsDNA antibody production in vitro, as well as spontaneous lupus in the MRL-Fas lpr/lpr lupus-prone mice. The idea is that the palindromic ODN is delivered to the autoreactive ds-DNA specific B cells via the B cell receptor for antigen, rather than through passive endocytosis resulting in compartment-specific inhibition and less toxicity.

ODNs with partial palindromes and short 3' or 5' overhangs (up to 3-4 nucleotides long) still possessed this preferential autoreactive B cell targeting. Additionally, because of their structure, these ODNs were also more effective in plasmacytoid dendritic cells. In contrast, in mouse naïve resting follicular B cells, as well as in human Namalwa B cells, these palindromic INH-ODNs were 10-30 fold less active, thus proving their selective cell and compartmental repertoire.

A. Synthesis

The inhibitory ODNs of the instant invention can encompass various chemical modifications and substitutions, in comparison to natural RNA and DNA, involving a phosphodiester internucleoside bridge, a (β-D-ribose unit and/or a natural nucleoside base (adenine, guanine, cytosine, thymine, uracil). Examples of chemical modifications are known to the skilled person and are described, for example, in Uhlmann et al. (1990); Synthesis and Properties & Synthesis and Analytical Techniques (1993); Crooke et al. (1996); and Hunziker et al. (1995). An oligonucleotide according to the invention may have one or more modifications, wherein each modification is located at a particular phosphodiester internucleoside bridge and/or at a particular β-D-ribose unit and/or at a particular natural nucleotide base position in comparison to an oligonucleotide of the same sequence which is composed of natural DNA or RNA.

For example, the oligonucleotides may include one or more modifications and wherein each modification is independently selected from:
  a) the replacement of a phosphodiester internucleoside bridge located at the 3' and/or the 5' end of a nucleoside by a modified internucleoside bridge;
  b) the replacement of phosphodiester bridge located at the 3' and/or the 5' end of a nucleoside by a dephospho bridge;
  c) the replacement of a sugar phosphate unit from the sugar phosphate backbone by another unit;
  d) the replacement of a β-D-ribose unit by a modified sugar unit; and
  e) the replacement of a natural nucleoside base by a modified nucleoside base.

The oligonucleotides may include modified internucleotide linkages, such as those described in a or b above. These modified linkages may be partially resistant to degradation (e.g., are stabilized). A "stabilized oligonucleotide molecule" shall mean an oligonucleotide that is relatively resistant to in vivo degradation (e.g., via an exo- or endonuclease) resulting from such modifications. Oligonucleotides having phosphorothioate linkages, in some embodiments, may provide maximal activity and protect the oligonucleotide from degradation by intracellular exo- and endo-nucleases.

A phosphodiester internucleoside bridge located at the 3' and/or the 5' end of a nucleoside can be replaced by a modified internucleoside bridge, wherein the modified internucleoside bridge is for example selected from phosphorothioate, phosphorodithioate, $NR^1R^2$-phosphoramidate, boranophosphate, α-hydroxybenzyl phosphonate, phosphate-$(C_1,-C_{21})$—O-alkyl ester, phosphate-$[(C_6-C_{12})$aryl-$(C_1-C_{21})$—O-alkyl]ester, $(C_1-C_8)$alkylphosphonate and/or $(C_6-C_{12})$arylphosphonate bridges, $(C_7-C_{12})$-α-hydroxymethyl-aryl (e.g., disclosed in WO 95/01363), wherein $(C_6-C_{12})$aryl, $(C_6-C_{20})$aryl and $(C_6-C_{14})$aryl are optionally substituted by halogen, alkyl, alkoxy, nitro, cyano, and where $R^1$ and $R^2$ are, independently of each other, hydrogen, $(C_1-C_{18})$-alkyl, $(C_6-C_{20})$-aryl, $(C_6-C_{14})$-aryl-$(C_1-C_8)$-alkyl, preferably hydrogen, $(C_1-C_8)$-alkyl, preferably $(C_1-C_4)$-alkyl and/or methoxyethyl, or $R^1$ and $R^2$ form, together with the nitrogen atom carrying them, a 5-6-membered heterocyclic ring which can additionally contain a further heteroatom from the group O, S and N.

The replacement of a phosphodiester bridge located at the 3' and/or the 5' end of a nucleoside by a dephospho bridge (dephospho bridges are described, for example, in Uhlmann and Peyman (1993), wherein a dephospho bridge is for example selected from the dephospho bridges formacetal, 3'-thioformacetal, methylhydroxylamine, oxime, methylenedimethyl-hydrazo, dimethylenesulfone and/or silyl groups.

A sugar phosphate unit (i.e., a β-D-ribose and phosphodiester internucleoside bridge together forming a sugar phosphate unit) from the sugar phosphate backbone (i.e., a sugar phosphate backbone is composed of sugar phosphate units) can be replaced by another unit, wherein the other unit is for example suitable to build up a "morpholino-derivative" oligomer (as described, for example, in Stirchak et al. (1989), that is, e.g., the replacement by a morpholino-derivative unit; or to build up a polyamide nucleic acid ("PNA"; as described for example, in Nielsen et al. (1994), that is, e.g., the replacement by a PNA backbone unit, e.g., by 2-aminoethylglycine. The oligonucleotide may have other carbohydrate backbone modifications and replacements, such as peptide nucleic acids with phosphate groups (PHONA), locked nucleic acids (LNA), and oligonucleotides having backbone sections with alkyl linkers or amino linkers. The alkyl linker may be branched or unbranched, substituted or unsubstituted, and chirally pure or a racemic mixture.

A β-ribose unit or a β-D-2'-deoxyribose unit can be replaced by a modified sugar unit, wherein the modified sugar unit is for example selected from β-D-ribose, α-D-2'-deoxyribose, L-2'-deoxyribose, 2'-F-2'-deoxyribose, 2'-F-arabinose, 2'-O—$(C_1$-$C_6)$alkyl-ribose, 2'-O-methylribose, 2'-O—$(C_2$-$C_6)$alkenyl-ribose, 2'40-$(C_1$-$C_6)$alkyl-O—$(C_1$-$C_6)$alkyl-ribose, 2'-$NH_2$-2'-deoxyribose, β-D-xylo-furanose, α-arabinofuranose, 2,4-dideoxy-β-D-erythrohexopyranose, and carbocyclic (described, for example, in Froehler (1992) and/or open-chain sugar analogs (described, for example, in Vandendriessche et al. (1993) and/or bicyclosugar analogs (described, for example, in Tarkov et al. (1993).

In some embodiments the sugar is 2'-O-methylribose, particularly for one or both nucleotides linked by a phosphodiester or phosphodiester-like internucleoside linkage.

Nucleic acids also include substituted purines and pyrimidines such as C-5 propyne pyrimidine and 7-deaza-7-substituted purine modified bases (Wagner et al., 1996). Purines and pyrimidines include but are not limited to adenine, cytosine, guanine, and thymine, and other naturally and non-naturally occurring nucleobases, substituted and unsubstituted aromatic moieties.

A modified base is any base which is chemically distinct from the naturally-occurring bases typically found in DNA and RNA such as T, C, G, A, and U, but which share basic chemical structures with these naturally-occurring bases. The modified nucleoside base may be, for example, selected from hypoxanthine, uracil, dihydrouracil, pseudouracil, 2-thiouracil, 4-thiouracil, 5-aminouracil, 5-$(C_1$-$C_6)$-alkyluracil, 5-$(C_2$-$C_6)$-alkenyluracil, 5-$(C_2$-$C_6)$-alkynyluracil, 5-(hydroxymethyl)uracil, 5-chlorouracil, 5-fluorouracil, 5-bromouracil, 5-hydroxycytosine, 5-$(C_1$-$C_6)$-alkylcytosine, 5-$(C_2$-$C_6)$-alkenylcytosine, 5-$(C_2$-$C_6)$-alkynylcytosine, 5-chlorocytosine, 5-fluorocytosine, 5-bromocytosine, $N^2$-dimethylguanine, 2,4-diamino-purine, 8-azapurine, a substituted 7-deazapurine, preferably 7-deaza-7-substituted and/or 7-deaza-8-substituted purine, 5-hydroxymethylcytosine, N4-alkylcytosine, e.g., N4-ethylcytosine, 5-hydroxydeoxycytidine, 5-hydroxymethyldeoxycytidine, N4-alkyldeoxycytidine, e.g., N4-ethyldeoxycytidine, 6-thiodeoxyguanosine, and deoxyribonucleosides of nitropyrrole, C5-propynylpyrimidine, and diaminopurine e.g., 2,6-diaminopurine, inosine, 5-methylcytosine, 2-aminopurine, 2-amino-6-chloropurine, hypoxanthine or other modifications of a natural nucleoside bases. This list is meant to be exemplary and is not to be interpreted to be limiting.

In particular formulas described herein modified bases may be incorporated. For instance a cytosine may be replaced with a modified cytosine. A modified cytosine as used herein is a naturally occurring or non-naturally occurring pyrimidine base analog of cytosine which can replace this base without impairing the immunostimulatory activity of the oligonucleotide. Modified cytosines include but are not limited to 5-substituted cytosines (e.g., 5-methyl-cytosine, 5-fluoro-cytosine, 5-chloro-cytosine, 5-bromo-cytosine, 5-iodo-cytosine, 5-hydroxy-cytosine, 5-hydroxymethyl-cytosine, 5-difluoromethyl-cytosine, and unsubstituted or substituted 5-alkynyl-cytosine), 6-substituted cytosines, N4-substituted cytosines (e.g., N4-ethyl-cytosine), 5-aza-cytosine, 2-mercapto-cytosine, isocytosine, pseudo-isocytosine, cytosine analogs with condensed ring systems (e.g., N,N'-propylene cytosine or phenoxazine), and uracil and its derivatives (e.g., 5-fluoro-uracil, 5-bromo-uracil, 5-bromovinyl-uracil, 4-thio-uracil, 5-hydroxy-uracil, 5-propynyl-uracil). Some of the preferred cytosines include 5-methyl-cytosine, 5-fluoro-cytosine, 5-hydroxy-cytosine, 5-hydroxymethyl-cytosine, and N4-ethyl-cytosine. In another embodiment of the invention, the cytosine base is substituted by a universal base (e.g., 3-nitropyrrole, P-base), an aromatic ring system (e.g., fluorobenzene or difluorobenzene) or a hydrogen atom (dSpacer).

A guanine may be replaced with a modified guanine base. A modified guanine as used herein is a naturally occurring or non-naturally occurring purine base analog of guanine which can replace this base without impairing the immunostimulatory activity of the oligonucleotide. Modified guanines include but are not limited to 7-deazaguanine, 7-deaza-7-substituted guanine (such as 7-deaza-7-($C_2$-$C_6$)alkynylguanine), 7-deaza-8-substituted guanine, hypoxanthine, N2-substituted guanines (e.g., N2-methyl-guanine), 5-amino-3-methyl-3H,6H-thiazolo[4,5-d]pyrimidine-2,7-dione, 2,6-diaminopurine, 2-aminopurine, purine, indole, adenine, substituted adenines (e.g., N6-methyl-adenine, 8-oxo-adenine), 8-substituted guanine (e.g., 8-hydroxyguanine and 8-bromoguanine), and 6-thioguanine. In another embodiment of the invention, the guanine base is substituted by a universal base (e.g., 4-methyl-indole, 5-nitro-indole, and K-base), an aromatic ring system (e.g., benzimidazole or dichloro-benzimidazole, 1-methyl-1H-[1,2,4]triazole-3-carboxylic acid amide) or a hydrogen atom (dSpacer).

For use in the instant invention, the oligonucleotides of the invention can be synthesized de novo using any of a number of procedures well known in the art, for example, the β-cyanoethyl phosphoramidite method (Beaucage et al., 1981); or the nucleoside H-phosphonate method (Garegg et al., 1986; Froehler et al., 1986; Garegg et al., 1986; Gaffney et al., 1988). These chemistries can be performed by a variety of automated nucleic acid synthesizers available in the market. These oligonucleotides are referred to as synthetic oligonucleotides. An isolated oligonucleotide generally refers to an oligonucleotide which is separated from components which it is normally associated with in nature. As an example, an isolated oligonucleotide may be one which is separated from a cell, from a nucleus, from mitochondria or from chromatin.

Modified backbones such as phosphorothioates may be synthesized using automated techniques employing either phosphoramidate or H-phosphonate chemistries. Aryl- and alkyl-phosphonates can be made, e.g., as described in U.S. Pat. No. 4,469,863; and alkylphosphotriesters (in which the charged oxygen moiety is alkylated as described in U.S. Pat. No. 5,023,243 and European Patent 092 574) can be prepared by automated solid phase synthesis using commercially available reagents. Methods for making other DNA backbone modifications and substitutions have been described (e.g., Uhlmann et al., 1990; Goodchild, 1990).

In each of the foregoing aspects of the invention, the composition can also further include a pharmaceutically acceptable carrier, such that the invention also provides pharmaceutical compositions containing the isolated inhibitory ODN of the invention.

The inhibitory ODN of the invention can also be used for the preparation of a medicament for use in treatment of a condition in a subject. The use according to this aspect of the invention involves the step of placing an effective amount of a composition of the invention in a pharmaceutically acceptable carrier.

B. Conjugates

In one aspect the invention provides a composition including a conjugate of an isolated immunoinhibitory nucleic acid molecule of the invention and an antigen or other therapeutic molecule. In one embodiment the antigen or other molecule is linked directly to the immunoinhibitory nucleic acid molecule of the invention, for example through a covalent bond. In one embodiment the antigen or other molecule is linked indirectly to the immunoinhibitory nucleic acid molecule of the invention, for example through a linker. When the antigen or other molecule of the conjugate is a polynucleotide encoding a peptide or polypeptide, the antigen or other molecule and the isolated immunoinhibitory nucleic acid molecule can be incorporated into a single expression vector. When the antigen or other molecule of the conjugate is a preformed polypeptide or polysaccharide, the antigen or other molecule and the isolated immunoinhibitory nucleic acid molecule can be linked using methods well known in the art.

The conjugate can include one or more isolated immunoinhibitory nucleic acid molecules of the invention. The conjugate can, alternatively or in addition, include one or more other molecules.

In one embodiment the conjugate includes an isolated immunoinhibitory nucleic acid molecule of the invention and a second molecule that is a TLR ligand or TLR agonist. More specifically, the TLR ligand or TLR agonist of the conjugate may be chosen from ligands and agonists of TLR7, TLR8, or TLR9. For example, in one embodiment an isolated immunoinhibitory nucleic acid molecule of the invention may be conjugated with an immunostimulatory CpG nucleic acid molecule. More particularly, in one embodiment an isolated TLR8 antagonist of the invention may be conjugated with an immunostimulatory CpG nucleic acid molecule. In one embodiment an isolated TLR7 antagonist of the invention may be conjugated with an immunostimulatory CpG nucleic acid molecule. In yet a further embodiment an isolated TLR7 antagonist of the invention and an isolated TLR8 antagonist of the invention may be conjugated with an immunostimulatory CpG nucleic acid molecule, wherein the TLR7 antagonist and the TLR8 antagonist may be present in a single molecular species or in separate molecular species.

As a further example of conjugates involving an isolated immunoinhibitory nucleic acid molecule of the invention and a second molecule that is a TLR ligand or TLR agonist, in one embodiment the conjugate includes a small molecule agonist of TLR7 or TLR8 (e.g., R-837 or R-848) and an isolated immunoinhibitory nucleic acid molecule of the invention (e.g., a TLR9 antagonist).

In some embodiments the conjugate includes two or more isolated immunoinhibitory nucleic acid molecules of the invention. The isolated immunoinhibitory nucleic acid molecules of the invention may be identical, may be different but selected from a single category (e.g., both TLR9 antagonists), or different and selected from different categories (e.g., a TLR9 antagonist and a TLR8 antagonist).

A conjugate that includes an isolated immunoinhibitory nucleic acid molecule of the invention and an antigen may be used to promote tolerance to the antigen. For example, it has been suggested that presentation of antigen to the immune system under circumstances which disfavor or prohibit development of a full immune response, e.g., by inhibiting costimulatory signals, can favor or induce so-called peripheral tolerance to the antigen. This type of tolerance is believed to reflect (clonal) anergy, in which antigen-specific T cells survive and are incapable of responding to the antigen upon subsequent presentation even in the context of adequate costimulation. Interestingly, it has been suggested that CpG ODN induce a signaling pathway in B cells that is most similar to CD40 costimulation, involving p38 and JNK, but not ERK-1 or ERK-2 (Yi et al., 1998; Lenert et al., 2003). It is also possible that the tolerance so induced may involve active immune suppression by so-called T-regulatory (Treg) cells. Treg cells may play an important role whenever the cytokine milieu is dominated by interleukin 10 (IL-10), i.e., the cytokine milieu is Th2-like; such a condition is believed to be favored by immunoinhibitory nucleic acid molecules of the invention. Whereas TLR agonists may block Treg suppressor activity (Pasare et al., 2003), TLR antagonists may be permissive to Treg activity.

C. Measuring Inhibitory Effects

The inhibitory effect of the inhibitory ODNs of the invention can be measured in vitro or in vivo. A basis for such measurement can involve, for example, comparison between stimulation of immune cells contacted with an appropriate source of TLR agonist, in the presence or absence of an appropriate source of inhibitory ODN. Stimulation that is reduced with inhibitory ODN compared with that without inhibitory ODN indicates an inhibitory effect of the inhibitory ODN. The inhibitory effect can be quantified and, if desired, used as the basis for screening or comparing candidate inhibitory ODN. Such screening and comparison can optionally be performed on a high throughput basis.

In one embodiment, a basis for measurement of the inhibitory effect of the inhibitory ODN of the invention in vitro can involve comparison between stimulation of TLR9-expressing cells contacted with an appropriate source of immunostimulatory CpG DNA, in the presence or absence of an appropriate source of inhibitory ODN. The TLR9-expressing cells can be cells that express TLR9 naturally, e.g., B cells or peripheral blood mononuclear cells (PBMC), or they can be cells that express TLR9 artificially, e.g., through transfection with a polynucleotide that encodes a TLR9.

Readouts for such measurements can be any suitable readout for assessing an effect, including TLR9 signaling, associated with immunostimulatory CpG DNA. For example, comparison can be made between B-cell apoptosis, cell cycle entry, cytokine secretion (e.g., IFN-α, IL-6, IL-12, TNF-α, IFN-γ, IP-10), CTL activity, or IgG2a. General methods for performing such measurements are well known in the art and include, for example, cell sorting, cytokine-specific enzyme-linked immunosorbent assay (ELISA), and chromium release cell lysis assay. As described in the Examples, the readout for such measurements can involve measurement of a marker, artificially introduced into a cell, for TLR9 signaling. In one embodiment the marker for TLR9 activity is expression of a gene placed under control of an NF-κB promoter, e.g., NF-κB-luciferase.

In one embodiment, a basis for measurement of the inhibitory effect of the inhibitory ODN of the invention in vitro can involve comparison between stimulation of TLR8-expressing cells contacted with an appropriate source of TLR8 agonist, such as R-848, in the presence or absence of an appropriate source of inhibitory ODN. The TLR8-expressing cells can be cells that express TLR8 naturally, e.g., monocytes or PBMC, or they can be cells that express TLR8 artificially, e.g., through transfection with a polynucleotide that encodes a TLR8.

Readouts for such measurements can be any suitable readout for assessing an effect, including TLR8 signaling, associated with a TLR8 agonist. As described in the Examples, the readout for such measurements can involve measurement of a marker, artificially introduced into a cell, for TLR8 signaling. In one embodiment the marker for TLR8 activity is expression of a gene placed under control of an NF-κB promoter, e.g., NF-κB-luciferase.

In one embodiment, a basis for measurement of the inhibitory effect of the inhibitory ODN of the invention in vitro can involve comparison between stimulation of TLR7-expressing cells contacted with an appropriate source of TLR7 agonist, such as R-848, in the presence or absence of an appropriate source of inhibitory ODN. The TLR7-expressing cells can be cells that express TLR7 naturally, e.g., B cells or PBMC, or they can be cells that express TLR7 artificially, e.g., through transfection with a polynucleotide that encodes a TLR7.

Readouts for such measurements can be any suitable readout for assessing an effect, including TLR7 signaling, associated with a TLR7 agonist. As described in the Examples, the readout for such measurements can involve measurement of a marker, artificially introduced into a cell, for TLR7 signaling. In one embodiment the marker for TLR7 activity is expression of a gene placed under control of an NF-κB promoter, e.g., NF-κB-luciferase.

In each of the foregoing aspects of the invention, the inhibitory ODN has a backbone that may be stabilized. In one embodiment the backbone is a sugar phosphate backbone that includes at least one phosphorothioate internucleotide linkage. In one embodiment the backbone is completely phosphorothioate.

IV. Use of Inhibitory ODNs

Further aspects of the invention relate to use of the inhibitory ODN of the invention. The oligonucleotides can be used alone or in combination with one another to inhibit signaling by TLR7, TLR8, or TLR9 individually or in any combination. Furthermore, the oligonucleotides can be used, alone or in combination with one another, in combination with an agonist or combination of agonists of any of TLR7, TLR8, or TLR9 to provide a combination inhibition/augmentation of signaling by any combination of TLR7, TLR8, and TLR9. The methods can be practiced in vitro and in vivo. Combinations of antagonists may involve separate molecules possessing the desired combination of antagonist motifs or they may involve single molecules possessing the desired combination of antagonist motifs. Similarly, combinations of agonists and antagonists may involve separate molecules possessing the desired combination of agonist and antagonist motifs or they may involve single molecules possessing the desired combination of agonist and antagonist motifs.

The invention in another aspect provides a method for reducing an immunostimulatory effect of a CpG nucleic acid molecule. The method involves the step of contacting an immune cell that is sensitive to a CpG nucleic acid molecule with an effective amount of an isolated immunoinhibitory nucleic acid molecule of the invention to reduce an immunostimulatory effect of the CpG nucleic acid molecule on the immune cell to a level below that which would occur without the contacting.

In one embodiment, the immunostimulatory effect that is inhibited is Th1-like skewing of an immune response. One feature of at least certain types of immunostimulatory CpG nucleic acids is their ability to skew an immune response toward a Th1-like profile and away from a Th2-like profile. This feature is believed to serve as a basis for the observed efficacy of immunostimulatory CpG nucleic acids as adjuvants, as agents for use in treatment of asthma and allergy, and the like. Thus, according to this embodiment of the invention, Th1-like skewing by immunostimulatory CpG nucleic acids can be inhibited. Such an effect may find use, for example, as an antidote to undesirable Th1-like skewing in the face of treatment with immunostimulatory CpG nucleic acids or exposure to immunostimulatory CpG nucleic acids through infection.

The step of contacting can take place before, essentially simultaneously with, or following contact of the cell with an appropriate source of immunostimulatory CpG nucleic acid molecule. For example, the contacting with the inhibitory ODN in certain embodiments takes place at least one day before the immune cell contacts a CpG nucleic acid molecule. As another example, the contacting with the inhibitory ODN in certain embodiments takes place at least one day after the immune cell contacts a CpG nucleic acid molecule. At least one day includes any time that is more than 24 hours and up to four weeks. In individual embodiments the at least one day is at least: 2 days, 3 days, 4 days, 5 days, 6 days, one week, two weeks, three weeks, or four weeks. In other embodiments the contacting with the inhibitory ODN can take place within 24 hours of the immune cell coming into contact with a CpG nucleic acid molecule.

It is believed that an effective amount of inhibitory ODN will generally be similar in amount to that of the source of CpG nucleic acid, although different amounts may be more or less effective. For use in vivo, an effective amount of inhibitory ODN may be higher.

In one embodiment the method is performed in vitro. In one embodiment the method is performed in vivo. Methods for assessing a reduction of an immunostimulatory effect of a CpG nucleic acid molecule are described above.

In one aspect, the invention provides a method for treating a condition associated with CpG-mediated immunostimulation in a subject. The method according to this aspect of the invention involves the step of administering to a subject having or at risk of developing a condition associated with CpG-mediated immunostimulation an effective amount of an isolated immunoinhibitory nucleic acid molecule of the invention to treat the condition. The method is useful whenever it is desirable to skew an immune response away from a Th1-like immune response. According to this aspect of the invention, inhibitory ODN of the invention may be used to treat any of a number of conditions that involve an innate immune response or a Th1-like immune response, including inflammation, acute and chronic allograft rejection, graft-versus-host disease (GvHD), certain autoimmune diseases, infection, and sepsis.

Autoimmune diseases can be generally classified as antibody-mediated, T-cell mediated, or a combination of antibody-mediated and T-cell mediated. Inhibitory ODN of the invention are believed to be most useful for treating various types of autoimmunity involving antibody-mediated or T-cell mediated immunity, including insulin-dependent (type I) diabetes mellitus, rheumatoid arthritis, multiple sclerosis, systemic lupus erythematosus (SLE), and inflammatory bowel disease (i.e., Crohn's disease and ulcerative colitis). Animal models for these autoimmune diseases are available and are useful for assessing the efficacy of inhibitory ODN in these diseases. Other autoimmune diseases include, without limitation, alopecia greata, acquired hemophilia, ankylosing spondylitis, antiphospholipid syndrome, autoimmune hepatitis, autoimmune hemolytic anemia, Beh.cedilla.et's syndrome, cardiomyopathy, celiac sprue dermatitis, chronic fatigue immune dysfunction syndrome (CFIDS), chronic inflammatory demyelinating polyneuropathy, Churg-Strauss syndrome, cicatricial pemphigoid, CREST syndrome, cold agglutinin disease, discoid lupus, essential mixed cryoglobulinemia, fibromyalgia, fibromyositis, Guillain-Barr syndrome, idiopathic pulmonary fibrosis, idiopathic thrombocytopenic purpura, IgA nephropathy, juvenile arthritis, lichen planus, myasthenia gravis, polyarteritis nodosa, polychondritis, polyglandular syndromes, dermatomyositis, primary agammaglobulinemia, primary biliary cirrhosis, psoriasis, Raynaud's phenomena, Reiter's syndrome, sarcoidosis, stiff-man syndrome, Takayasu arthritis, temporal arteritis/giant cell arteritis, uveitis, vasculitis, and vitiligo.

In several autoimmune diseases antibodies to self antigens are frequently observed. For example for systemic lupus erythematosus autoantibodies have been described to single-stranded and double-stranded DNA or RNA (Vallin et al., 1999; Hoet et al., 1999; ven Venrooij, 1990). The levels of autoantibodies found in the serum of autoimmune patients very often are found to correlate with disease severity. The pattern of autoantibodies that arise, e.g., in human SLE, suggest that intact macromolecular particles, such as RNA- or DNA-containing complexes, could themselves be immunogenic and anti-nucleic acid antibodies could therefore arise (Lotz et al., 1992; Mohan et al., 1993). Such DNA or RNA released from, e.g., apoptotic cells or DNA- or RNA-containing microbes present in serum of autoimmune patients, could be responsible for inflammation that contributes to the autoimmune disease (Fatenejad, 1994; Malmegrim et al., 2002; Newkirk et al., 2001). Indeed CpG-containing sequences could be identified from SLE serum that induces an efficient immune response dominated by IFN-α. secretion that is thought to contribute the development of to autoimmune diseases (Magnusson et al., 2001; Ronnblom et al., 2001). In addition, the epitopes for anti-RNA antibodies could be identified and are composed of G,U-rich sequences (Tsai et al., 1992; Tsai et al., 1993). G,U-rich sequences appear to be natural ligands for TLR7 and TLR8 and, therefore, can mediate immune stimulatory responses that in principle could contribute to autoimmune diseases or the development of autoimmune diseases (PCT/US03/10406). Given the importance of immune stimulation mediated by serum CpG DNA or G,U-rich RNA that are targets for autoantibodies, the present invention provides a method for treating a condition associated with CpG DNA- or RNA-mediated immunostimulation in a subject having or being at risk of having an autoimmune disease.

Infections refer to any condition in which there is an abnormal collection or population of viable intracellular or extracellular microbes in a subject. Various types of microbes can cause infection, including microbes that are bacteria, microbes that are viruses, microbes that are fungi, and microbes that are parasites.

Bacteria include, but are not limited to, *Pasteurella* species, *Staphylococci* species, *Streptococcus* species, *Escherichia coli, Pseudomonas* species, and *Salmonella* species. Specific examples of infectious bacteria include but are not limited to, *Helicobacter pyloris, Borrelia burgdorferi, Legionella pneumophilia, Mycobacteria* sp. (e.g., *M. tuberculosis, M. avium, M. intracellulare, M. kansasii, M. gordonae*), *Staphylococcus aureus, Neisseria gonorrhoeae, Neisseria meningitidis, Listeria monocytogenes, Streptococcus pyogenes* (Group A *Streptococcus*), *Streptococcus agalactiae* (Group B *Streptococcus*), *Streptococcus viridans* group, *Streptococcus faecalis, Streptococcus bovis, Streptococcus anaerobic* sp., *Streptococcus pneumoniae*, pathogenic *Campylobacter* sp., *Enterococcus* sp., *Haemophilus influenzae, Bacillus anthracis, Corynebacterium diphtheriae, Corynebacterium* sp., *Erysipelothrix rhusiopathiae, Clostridium perfringens, Clostridium tetani, Enterobacter aerogenes, Klebsiella pneumoniae, Pasturella multocida, Bacteroides* sp., *Fusobacte-*

*rium nucleatum, Streptobacillus moniliformis, Treponema pallidum, Treponema pertenue, Leptospira, Rickettsia*, and *Actinomyces israelii*.

Examples of viruses that have been found in humans include but are not limited to: Retroviridae (e.g., human immunodeficiency viruses, such as HIV-1 (also referred to as HTLV-III, LAV or HTLV-III/LAV, or HIV-III; and other isolates, such as HIV-LP; Picornaviridae (e.g., polio viruses, hepatitis A virus; enteroviruses, human Coxsackie viruses, rhinoviruses, echoviruses); Calciviridae (e.g., strains that cause gastroenteritis); Togaviridae (e.g., equine encephalitis viruses, rubella viruses); Flaviviridae (e.g., dengue viruses, encephalitis viruses, yellow fever viruses); Coronaviridae (e.g., coronaviruses); Rhabdoviridae (e.g., vesicular stomatitis viruses, rabies viruses); Filoviridae (e.g., ebola viruses); Paramyxoviridae (e.g., parainfluenza viruses, mumps virus, measles virus, respiratory syncytial virus); Orthomyxoviridae (e.g., influenza viruses); Bunyaviridae (e.g., Hantaan viruses, bunga viruses, phleboviruses and Nairo viruses); Arenaviridae (hemorrhagic fever viruses); Reoviridae (e.g., reoviruses, orbiviurses and rotaviruses); Bornaviridae; Hepadnaviridae (Hepatitis B virus); Parvoviridae (parvoviruses); Papovaviridae (papilloma viruses, polyoma viruses); Adenoviridae (most adenoviruses); Herpesviridae (herpes simplex virus (HSV) 1 and 2, varicella zoster virus, cytomegalovirus (CMV), herpes virus; Poxyiridae (variola viruses, vaccinia viruses, pox viruses); and Iridoviridae (e.g., African swine fever virus); and unclassified viruses (e.g., the agent of delta hepatitis (thought to be a defective satellite of hepatitis B virus), Hepatitis C; Norwalk and related viruses, and astroviruses).

Fungi include yeasts and molds. Examples of fungi include without limitation *Aspergillus* spp including *Aspergillus fumigatus, Blastomyces dermatitidis, Candida* spp. including *Candida albicans, Coccidioides immitis, Cryptococcus neoformans, Histoplasma capsulatum, Pneumocystis carinii, Rhizomucor* spp., and *Rhizopus* spp.

Other infectious organisms (i.e., protists) include *Plasmodium* spp., such as *Plasmodium falciparum, Plasmodium malariae, Plasmodium ovale*, and *Plasmodium vivax* and *Toxoplasma gondii*. Blood-borne and/or tissue parasites include *Plasmodium* spp., *Babesia microti, Babesia divergens, Chlamydia trachomatis, Leishmania tropica, Leishmania* spp., *Leishmania braziliensis, Leishmania donovani, Trypanosoma gambiense* and *Trypanosoma rhodesiense* (African sleeping sickness), *Trypanosoma cruzi* (Chagas' disease), and *Toxoplasma gondii*.

Other medically relevant microorganisms have been described extensively in the literature, e.g., see Medical Microbiology (1983), the entire contents of which is hereby incorporated by reference.

A. Dosing and Administration

The inhibitory ODN of the invention can be used alone, in combination with themselves, in combination with another agent, or in combination with themselves and with another agent. In addition to the conjugates described herein, the inhibitory ODN in combination with another agent can also be separate compositions that are used together to achieve a desired effect. For example, an inhibitory ODN and a second agent can be mixed together and administered to a subject or placed in contact with a cell as a combination. As another example, an inhibitory ODN and a second agent can be administered to a subject or placed in contact with a cell at different times. As yet another example, an inhibitory ODN and a second agent can be administered to a subject at different sites of administration.

The inhibitory ODN and/or the antigen and/or other therapeutics may be administered alone (e.g., in saline or buffer) or using any delivery vehicle known in the art. For instance the following delivery vehicles have been described: cochleates (Gould-Fogerite et al., 1994); emulsomes (Vancott et al., 1998, Lowell et al., 1997); ISCOMs (Mowat et al., 1993, Carlsson et al., 1991, Hu et al., 1998, Morein et al., 1999); liposomes (Childers et al., 1999, Michalek et al., 1989, 1992, de Haan 1995a, 1995b); live bacterial vectors (e.g., *Salmonella, Escherichia coli, bacillus* Calmette-Gurin, *Shigella, Lactobacillus*) (Hone et al., 1996, Pouwels et al., 1998, Chatfield et al., 1993, Stover et al., 1991, Nugent et al., 1998); live viral vectors (e.g., Vaccinia, adenovirus, Herpes simplex) (Gallichan et al., 1993, 1995, Moss et al., 1996, Nugent et al., 1998, Flexner et al., 1988, Morrow et al., 1999); microspheres (Gupta et al., 1998, Jones et al., 1996, Maloy et al., 1994, Moore et al., 1995, Eldridge et al., 1989); nucleic acid vaccines (Fynan et al., 1993, Kuklin et al., 1997, Sasaki et al., 1998, Okada et al., 1997, Ishii et al., 1997); polymers (e.g., carboxymethylcellulose, chitosan) (Hamajima et al., 1998, Jabbal-Gill et al., 1998); polymer rings (Wyatt et al., 1998); proteosomes (Vancott et al., 1998, Lowell et al., 1988, 1996, 1997); transgenic plants (Tacket et al., 1998, Mason et al., 1998, Haq et al., 1995); Virosomes (Gluck et al., 1992, Mengiardi et al., 1995, Cryz et al., 1998); virus-like particles (Jiang et al., 1999, Leibl et al., 1998). Other delivery vehicles are known in the art.

As mentioned above, the term "effective amount" refers generally to the amount necessary or sufficient to realize a desired biologic effect. Combined with the teachings provided herein, by choosing among the various active compounds and weighing factors such as potency, relative bioavailability, patient body weight, severity of adverse side-effects and preferred mode of administration, an effective prophylactic or therapeutic treatment regimen can be planned which does not cause substantial toxicity and yet is entirely effective to treat the particular subject. The effective amount for any particular application can vary depending on such factors as the disease or condition being treated, the particular oligonucleotide being administered, the size of the subject, or the severity of the disease or condition. One of ordinary skill in the art can empirically determine the effective amount of a particular inhibitory ODN and/or antigen and/or other therapeutic agent without necessitating undue experimentation.

Subject doses of the compounds described herein for systemic or local delivery typically range from about 10 ng to 10 mg per administration, which depending on the application could be given daily, weekly, or monthly and any other amount of time therebetween or as otherwise required. More typically systemic or local doses range from about 1 µg to 1 mg per administration, and most typically from about 10 µg to 100 µg, with 2-4 administrations being spaced days or weeks apart. Higher doses may be required for parenteral administration. In some embodiments, however, parenteral doses for these purposes may be used in a range of 5- to 10,000-times higher than the typical doses described above.

For any compound described herein the therapeutically effective amount can be initially determined from animal models. The applied dose can be adjusted based on the relative bioavailability and potency of the administered compound. Adjusting the dose to achieve maximal efficacy based on the methods described above and other methods as are well-known in the art is well within the capabilities of the ordinarily skilled artisan.

B. Route of Administration

For clinical use the inhibitory ODN of the invention can be administered alone or formulated as a delivery complex via any suitable route of administration that is effective to achieve the desired therapeutic result. Routes of administration include enteral and parenteral routes of administration. Examples of enteral routes of administration include oral, gastric, intestinal, and rectal. Nonlimiting examples of parenteral routes of administration include intravenous, intramuscular, subcutaneous, intraperitoneal, intrathecal, local injection, topical, nasal, mucosal, and pulmonary.

C. Formulation

The inhibitory ODN of the invention may be directly administered to the subject or may be administered in conjunction with a nucleic acid delivery complex. A nucleic acid delivery complex shall mean a nucleic acid molecule associated with (e.g., ionically or covalently bound to; or encapsulated within) a targeting means (e.g., a molecule that results in higher affinity binding to target cell. Examples of nucleic acid delivery complexes include nucleic acids associated with a sterol (e.g., cholesterol), a lipid (e.g., a cationic lipid, virosome or liposome), or a target cell specific binding agent (e.g., a ligand recognized by target cell specific receptor). Preferred complexes may be sufficiently stable in vivo to prevent significant uncoupling prior to internalization by the target cell. However, the complex can be cleavable under appropriate conditions within the cell so that the oligonucleotide is released in a functional form.

For oral administration, the compounds (i.e., inhibitory ODN, antigens and/or other therapeutic agents) can be formulated readily by combining the active compound(s) with pharmaceutically acceptable carriers well known in the art. Such carriers enable the compounds of the invention to be formulated as tablets, pills, dragees, capsules, liquids, gels, syrups, slurries, suspensions and the like, for oral ingestion by a subject to be treated. Pharmaceutical preparations for oral use can be obtained as solid excipient, optionally grinding a resulting mixture, and processing the mixture of granules, after adding suitable auxiliaries, if desired, to obtain tablets or dragee cores. Suitable excipients are, in particular, fillers such as sugars, including lactose, sucrose, mannitol, or sorbitol; cellulose preparations such as, for example, maize starch, wheat starch, rice starch, potato starch, gelatin, gum tragacanth, methyl cellulose, hydroxypropylmethyl-cellulose, sodium carboxymethylcellulose, and/or polyvinylpyrrolidone (PVP). If desired, disintegrating agents may be added, such as the cross-linked polyvinyl pyrrolidone, agar, or alginic acid or a salt thereof such as sodium alginate. Optionally the oral formulations may also be formulated in saline or buffers for neutralizing internal acid conditions or may be administered without any carriers.

Dragee cores are provided with suitable coatings. For this purpose, concentrated sugar solutions may be used, which may optionally contain gum arabic, talc, polyvinyl pyrrolidone, carbopol gel, polyethylene glycol, and/or titanium dioxide, lacquer solutions, and suitable organic solvents or solvent mixtures. Dyestuffs or pigments may be added to the tablets or dragee coatings for identification or to characterize different combinations of active compound doses.

Pharmaceutical preparations which can be used orally include push-fit capsules made of gelatin, as well as soft, sealed capsules made of gelatin and a plasticizer, such as glycerol or sorbitol. The push-fit capsules can contain the active ingredients in admixture with filler such as lactose, binders such as starches, and/or lubricants such as talc or magnesium stearate and, optionally, stabilizers. In soft capsules, the active compounds may be dissolved or suspended in suitable liquids, such as fatty oils, liquid paraffin, or liquid polyethylene glycols. In addition, stabilizers may be added. Microspheres formulated for oral administration may also be used. Such microspheres have been well defined in the art. All formulations for oral administration should be in dosages suitable for such administration.

For buccal administration, the compositions may take the form of tablets or lozenges formulated in conventional manner.

The compounds may be administered by inhalation to pulmonary tract, especially the bronchi and more particularly into the alveoli of the deep lung, using standard inhalation devices. The compounds may be delivered in the form of an aerosol spray presentation from pressurized packs or a nebulizer, with the use of a suitable propellant, e.g., dichlorodifluoromethane, trichlorofluoromethane, dichlorotetrafluoroethane, carbon dioxide, or other suitable gas. In the case of a pressurized aerosol, the dosage unit may be determined by providing a valve to deliver a metered amount. An inhalation apparatus may be used to deliver the compounds to a subject. An inhalation apparatus, as used herein, is any device for administering an aerosol, such as dry powdered form of the compounds. This type of equipment is well known in the art and has been described in detail, such as that description found in Remington's: The Science and Practice of Pharmacy (1995). Many U.S. patents also describe inhalation devices, such as U.S. Pat. No. 6,116,237.

"Powder" as used herein refers to a composition that consists of finely dispersed solid particles. Preferably the compounds are relatively free flowing and capable of being dispersed in an inhalation device and subsequently inhaled by a subject so that the compounds reach the lungs to permit penetration into the alveoli. A "dry powder" refers to a powder composition that has a moisture content such that the particles are readily dispersible in an inhalation device to form an aerosol. The moisture content is generally below about 10% by weight (% w) water, and in some embodiments is below about 5% w and preferably less than about 3% w. The powder may be formulated with polymers or optionally may be formulated with other materials such as liposomes, albumin and/or other carriers.

Aerosol dosage and delivery systems may be selected for a particular therapeutic application by one of skill in the art, such as described, for example in Gonda (1990) and in Moren (1985).

The compounds, when it is desirable to deliver them systemically, may be formulated for parenteral administration by injection, e.g., by bolus injection or continuous infusion. Formulations for injection may be presented in unit dosage form, e.g., in ampoules or in multi-dose containers, with an added preservative. The compositions may take such forms as suspensions, solutions or emulsions in oily or aqueous vehicles, and may contain formulatory agents such as suspending, stabilizing and/or dispersing agents.

Pharmaceutical formulations for parenteral administration include aqueous solutions of the active compounds in water-soluble form. Additionally, suspensions of the active compounds may be prepared as appropriate oily injection suspensions. Suitable lipophilic solvents or vehicles include fatty oils such as sesame oil, or synthetic fatty acid esters, such as ethyl oleate or triglycerides, or liposomes. Aqueous injection suspensions may contain substances which increase the viscosity of the suspension, such as sodium carboxymethyl cellulose, sorbitol, or dextran. Optionally, the suspension may also contain suitable stabilizers or agents which increase the solubility of the compounds to allow for the preparation of highly concentrated solutions.

Alternatively, the active compounds may be in powder form for constitution with a suitable vehicle, e.g., sterile pyrogen-free water, before use.

The compounds may also be formulated in rectal or vaginal compositions such as suppositories or retention enemas, e.g., containing conventional suppository bases such as cocoa butter or other glycerides.

In addition to the formulations described previously, the compounds may also be formulated as a depot preparation. Such long acting formulations may be formulated with suitable polymeric or hydrophobic materials (for example as an emulsion in an acceptable oil) or ion exchange resins, or as sparingly soluble derivatives, for example, as a sparingly soluble salt.

The pharmaceutical compositions also may include suitable solid or gel phase carriers or excipients. Examples of such carriers or excipients include but are not limited to calcium carbonate, calcium phosphate, various sugars, starches, cellulose derivatives, gelatin, and polymers such as polyethylene glycols.

Suitable liquid or solid pharmaceutical preparation forms are, for example, aqueous or saline solutions for inhalation, microencapsulated, encochleated, coated onto microscopic gold particles, contained in liposomes, nebulized, aerosols, pellets for implantation into the skin, or dried onto a sharp object to be scratched into the skin. The pharmaceutical compositions also include granules, powders, tablets, coated tablets, (micro)capsules, suppositories, syrups, emulsions, suspensions, creams, drops or preparations with protracted release of active compounds, in whose preparation excipients and additives and/or auxiliaries such as disintegrants, binders, coating agents, swelling agents, lubricants, flavorings, sweeteners or solubilizers are customarily used as described above. The pharmaceutical compositions are suitable for use in a variety of drug delivery systems. For a brief review of methods for drug delivery, see Langer (1990), which is incorporated herein by reference.

The inhibitory ODN and optionally other therapeutics and/or antigens may be administered per se (neat) or in the form of a pharmaceutically acceptable salt. When used in medicine the salts should be pharmaceutically acceptable, but non-pharmaceutically acceptable salts may conveniently be used to prepare pharmaceutically acceptable salts thereof. Such salts include, but are not limited to, those prepared from the following acids: hydrochloric, hydrobromic, sulphuric, nitric, phosphoric, maleic, acetic, salicylic, p-toluene sulphonic, tartaric, citric, methane sulphonic, formic, malonic, succinic, naphthalene-2-sulphonic, and benzene sulphonic. Also, such salts can be prepared as alkaline metal or alkaline earth salts, such as sodium, potassium or calcium salts of the carboxylic acid group.

Suitable buffering agents include: acetic acid and a salt (1-2% w/v); citric acid and a salt (1-3% w/v); boric acid and a salt (0.5-2.5% w/v); and phosphoric acid and a salt (0.8-2% w/v). Suitable preservatives include benzalkonium chloride (0.003-0.03% w/v); chlorobutanol (0.3-0.9% w/v); parabens (0.01-0.25% w/v) and thimerosal (0.004-0.02% w/v).

The pharmaceutical compositions of the invention contain an effective amount of an inhibitory ODN and optionally antigens and/or other therapeutic agents optionally included in a pharmaceutically acceptable carrier. The term pharmaceutically acceptable carrier means one or more compatible solid or liquid filler, diluents or encapsulating substances which are suitable for administration to a human or other vertebrate animal. The term carrier denotes an organic or inorganic ingredient, natural or synthetic, with which the active ingredient is combined to facilitate the application. The components of the pharmaceutical compositions also are capable of being comingled with the compounds of the present invention, and with each other, in a manner such that there is no interaction which would substantially impair the desired pharmaceutical efficiency.

V. EXAMPLES

The following examples are included to demonstrate preferred embodiments of the invention. It should be appreciated by those of skill in the art that the techniques disclosed in the examples which follow represent techniques discovered by the inventor to function well in the practice of the invention, and thus can be considered to constitute preferred modes for its practice. However, those of skill in the art should, in light of the present disclosure, appreciate that many changes can be made in the specific embodiments which are disclosed and still obtain a like or similar result without departing from the spirit and scope of the invention.

Example 1

A major function of the innate immune system defending us against bacteria and viruses is the recognition of molecules made by these microbes that we do not make, performed by Toll-like receptors (TLRs). For example, TLR9 is activated by oligonucleotides (ODN) sharing certain sequence features with bacterial DNA. The inventors have previously defined and published the sequence characteristics of a closely related class of ODN that inhibit ODN-activation of mouse TLR9, the inhibitory (IN-)ODN. This invention relates to the discovery that particular 4-5 base extensions at the 5' and of previously published IN-ODN sequences enhance their potency 2 to 6-fold in cells expressing human TLR9, and thus more completely inhibit activation of immune cells at the same concentration range. In autoimmune diseases where TLR9 activation plays an inciting role, interference with TLR9 activation may be therapeutic, and also in combatting excessive activation TLR9, such as in septic shock.

Methods. C57bl/6 mice were the source of spleen B cells purified by negative selection. Human B cells were represented by the Namalwa B cell line, and B cells isolated by negative selection from peripheral blood. Human embryonic kidney (HEK) cells transfected with human or mouse TLR9 also expressed a transgene for luciferase linked to an NFκB-responsive promoter. Conditions were chosen to provide the minimum stimulation for a maximal response: 100 nM of the single motif ODN 2084 for mouse B cells and 100 nM of the 3-motif ODN 2006 for human B cells in the same set of 3 or more experiments. IN-ODN at a range of concentrations including the 50% inhibition point were added at culture initiation. Assays included apoptosis protection and cell cycle entry into G1 (acridine orange flow cytometry), and IL6 secretion by ELISA for mouse cells, CD86 upregulation for Namalwa cells and NFκB by luminescence for HEK/TLR9 cells. Inhibitory activity was calculated by comparison to the activity of the prototype inhibitory ODN 2114 in the same set of 3 or more experiments. By performing t-tests on a sample of triplicate experiments, we showed that approximately a 2-fold difference in activity is significant at p=0.005, as appropriate for the large number of comparisons.

Results. First, the inventors sought to convert the prototype ST-ODN for human cells, 2006, into an IN-ODN by making similar G substitutions in one or all of the CpG motifs. When none of these variants exerted more than 5% of the inhibitory activity of ODN 2114, the inventors instead examined a series of variants of the 2114 sequence in HEK/human TLR9 and Namalwa cells to compare with the HEK/mouse LTR and mouse spleen B cells (Table 1). Changes in hotspots 1 and 3 reduced activity in both human and mouse cells (4115, 4008, 4005). 2310, which was neutral in mouse was also neutral in human. Variant 4266 was the best example of a sequence with different effects in mouse and human, and since this difference was evident in HEK cells, we can attribute it to species differences in TLR9.

A more extensive series of 2114 variants was examined in both HEK/hu and Namalwa cells (Table 2). Consistently, the same base hotspot changes that drastically reduced activity in mouse spleen B cells (2) also did so in both types of human cells. ODN 4145's lack of activity proved the requirement for 3 G's at hotspot 3 in mouse cells, a property shared by human cells. For most IN-ODN's including 2114, inhibitory potency was about 3× greater in HEK cells. Truncation of position −7 enhanced activity (4033) only in Namlawa cells, but loss of 4 bases at the 5' end (4031) decreased activity, and compensated for the 3' truncation effect (4171). IN-ODN's 3- to 6-fold stronger than 2114 were achieved with 3' additions duplicating hotspot 1 with an A spacer at position −8 (4191). Deleting the 5' T, and use of TCG in place of TCC to match the hotspot 1 sequence preferred in ST-ODN by human cells increased activity slightly over 4191. Curiously, the AA for CC substitution at −5, −6, so deadly in hotspot of 2114 (4141), still reduced activity in the elongated version (4350), while the same substitution at −10, −11 (4349) did not. Further duplication (3 "hotspot 1" in 4351) had no further effect. Considering both cell types 4347 (18 bases) and 4348 (19 bases) are the strongest IN-ODN discovered for human cells (Table 2). The inventors also tested the sequences H154, 1502 and the "triple telomere" sequence 4000, described by Klinman et al., together with the variants the inventors proposed to enhance their activity (Table 2). None of these performed as well as 2114 in human cells.

Potency comparison in mouse B cells between IN-ODN with the same sequence but phosphodiester instead of nuclease-resistant phosphothioate backbones showed the latter to confer a 2-log advantage in potency for ST-ODN and a 3-log advantage for IN-ODN. Base substitutions in the hotspots curtailed IN-ODN activity with either backbone but these differences were greater with the O-backbone.

Summary. ODN which share with strong stimulatory ODN the CC at positions −5, −6, and bases other than C at positions −2, −3, may be inhibitor in mouse cells if they possess 3 consecutive G's in the interval +1 to +4 in place of CGTT. This report documents the search for strong inhibitory sequences in human B cells, concluding that the majority of strong IN-ODN derived from mouse studies including the prototype 2114 also work in human B cells, and that with few exceptions, the same set of rules relating to sequence activity apply in both species. The inventors also show in mouse cells that these rules tend to apply to ODN with phosphodiester as well as phosphorothioate backbones, although the latter are much more potent. The inventors describe a similar set of ODN's which appear to be the strongest inhibitors for human B cells, using HEK cells transfected with human TLR9 and the Namlawa B cell line.

TABLE 1

IN-ODN Activity in Human (hu) and Mouse (mo) Cells

|      | HEK/hu (%) | Namalwa/hu | Blood B/hu | HEK/mo | Mo B |
|------|------|------|------|------|------|
| 2114 | 100  | 100  | 100  | 100  | 100  |
| 4266 | 12.5 | 10   | 19   | 1100 | 119  |
| 4171 | 75   | 100  | 45   | 280  | 23   |
| 4115 | 1.5  | 5    | 9    | 18   | 23   |
| 4008 | 1.5  | 3    | 3    | 6    | 50   |
| 4005 | 5    | 17   | 12   | 1.4  | 26   |
| 2310 | 0.3  | 0.2  | 0.5  | 0.3  | 0.2  |

TABLE 2

Sequence/Activity Relationship for IN-ODN in Human Cells

| Variant Type | # | Bold indicates difference from 2114 seq. | | HEK/hu % | Namalwa % |
|---|---|---|---|---|---|
|              | 2008 | TCCTGGCGGGGAAGT | (SEQ ID NO: 11) | 60  | 150 |
| Hotspot 1    | 4115 | TACTGGAGGGGAAGT | (SEQ ID NO: 12) | 1.5 | 2.3 |
|              | 4110 | TCATGGAGGGGAAGT | (SEQ ID NO: 13) | 0.3 | 5   |
|              | 4143 | TAATGGAGGGGAAGT | (SEQ ID NO: 14) | 0.5 | 0.8 |
| Hotspot 2    | 4017 | TCCTGCAGGGGAAGT | (SEQ ID NO: 15) | 2.8 | 47  |
|              | 4141 | TCCTCCAGGGGAAGT | (SEQ ID NO: 16) | 0.8 | 4.8 |
| Hotspot 3    | 4005 | TCCTGGAGTGGAAGT | (SEQ ID NO: 17) | 5   | 26  |
|              | 4008 | TCCTGGAGGTGAAGT | (SEQ ID NO: 18) | 1.5 | 3   |
|              | 4004 | TCCTGGAGCGGAAGT | (SEQ ID NO: 19) | 0.3 | 2.8 |
|              | 4007 | TCCTGGAGGCGAAGT | (SEQ ID NO: 20) | 0.8 | 3.6 |
|              | 4145 | TCCTGGACGCAAGT | (SEQ ID NO: 21) | 0.1 | 1   |
| Truncation   | 4031 | TCCTGGAGGGG---- | (SEQ ID NO: 22) | 9.7 | 42  |
|              | 4033 | -CCTGGAGGGGAAGT | (SEQ ID NO: 23) | 113 | 625 |
|              | 4171 | -CCTGGAGGGG---- | (SEQ ID NO: 24) | 101 | 100 |
|              | 4028 | --CTGGAGGGGAAGT | (SEQ ID NO: 25) | 0.4 | 5.9 |
|              | 4266 | -CCAGGAGGGGAAGT | (SEQ ID NO: 26) | 15  | 10  |
| 5' Additions | 4352 | TCCTTCCTGGAGGGGAAGT | (SEQ ID NO: 27) | 90  | 282 |
| Published    | 4191 | TCCTATCCTGGAGGGGAAG | (SEQ ID NO: 28) | 229 | 404 |
|              | 4351 | (TCCTA)TCCTGGAGGGGAAG | (SEQ ID NO: 29) | 338 | 310 |

TABLE 2-continued

Sequence/Activity Relationship for IN-ODN in Human Cells

| Variant Type | # Bold indicates difference from 2114 seq. | | HEK/hu % | Namalwa % |
|---|---|---|---|---|
| | 4348 TCGTATCCTGGAGGGGAAG | (SEQ ID NO: 30) | 338 | 660 |
| | 4349 TAATATCCTGGAGGGGAAG | (SEQ ID NO: 31) | 193 | 585 |
| | 4347 -CCTATCCTGGAGGGGAAG | (SEQ ID NO: 32) | 405 | 534 |
| Published | 4350 TCCTATAATGGAGGGGAAG | (SEQ ID NO: 33) | 16 | 53 |
| Center | H154 (5)-CCTCAAGCTTGAGGGG | (SEQ ID NO: 34) | 26 | 33 |
| Sequences | 4248 -CCTCAAGGGTGAGGGG | (SEQ ID NO: 35) | 4.7 | 47 |
| | 1502 (5)GAGCAAGCTGGACCTTCCAT | (SEQ ID NO: 36) | 2.1 | 1.9 |
| | 4245 GACCAAGCGGGACCTTCCAT | (SEQ ID NO: 37) | 5.8 | 5.0 |
| | 4000 (4)TTAGGGTTAGGGTTAGGG | (SEQ ID NO: 38) | 2.6 | 1.6 |

All of the compositions and methods disclosed and claimed herein can be made and executed without undue experimentation in light of the present disclosure. While the compositions and methods of this invention have been described in terms of preferred embodiments, it will be apparent to those of skill in the art that variations may be applied to the compositions and methods and in the steps or in the sequence of steps of the method described herein without departing from the concept, spirit and scope of the invention. More specifically, it will be apparent that certain agents which are both chemically and physiologically related may be substituted for the agents described herein while the same or similar results would be achieved. All such similar substitutes and modifications apparent to those skilled in the art are deemed to be within the spirit, scope and concept of the invention as defined by the appended claims.

VI. REFERENCES

The following references, to the extent that they provide exemplary procedural or other details supplementary to those set forth herein, are specifically incorporated herein by reference.

U.S. Pat. No. 4,469,863
U.S. Pat. No. 5,023,243
U.S. Pat. No. 6,116,237
U.S. Pat. No. 6,194,388
U.S. Pat. No. 6,207,646
U.S. Pat. No. 6,218,371
U.S. Pat. No. 6,239,116
U.S. Pat. No. 6,339,068
U.S. Pat. No. 6,406,705
U.S. Pat. No. 6,429,199
Aderem et al., *Nature*, 406:782-787, 2000.
Alexopoulou et al., *Nature*, 413:732-738, 2001.
Aliprantis et al., *Science*, 285:736-739, 1999.
Bauer et al., *Proc. Natl. Acad. Sci. USA*, 98:9237-9242, 2001.
Beaucage et al., *Tetrahedron Lett.*, 22:1859, 1981.
Carlsson et al., *Vaccine*, 9(8):577-580, 1991.
Chatfield et al., *FEMS Immunol Med Microbiol.*, 7(1):1-7, 1993.
Childers et al., *Infect. Immun.*, 67(2):618-623, 1999.
Chuang et al., *Eur. Cytokine Netw.*, 11:372-388, 2000.
Crooke et al., *Annu. Rev. Pharmacol. Toxicol.*, 36:107-129, 1996.
Cryz et al., *Dev. Biol. Stand.*, 92:219-223, 1998.
de Haan et al., *Vaccine*, 13(14):1320-1324, 1995a.
de Haan et al., *Vaccine*, 13(2):155-162, 1995b.
Eldridge et al., *Curr. Top. Microbiol. Immunol.*, 146:59-66, 1989.
European Patent 092 574
Fatenejad, *J. Immunol.*, 152:5523-5531, 1994.
Flexner et al., *Nature*, 335(6187):259-262, 1988.
Froehler et al., *Nucleic Acids Res.*, 14:5399-5407, 1986.
Froehler, *J. Am. Chem. Soc.*, 114:8320, 1992.
Fynan et al., *Proc. Natl. Acad. Sci. USA*, 90(24):11478-11482, 1993.
Gaffney et al., *Tetrahedron Lett.*, 29:2619-2622, 1988.
Gallichan et al., *J. Infect. Dis.*, 168(3):622-629 1993.
Gallichan et al., *Vaccine*, 13(16):1589-1595, 1995.
Garegg et al., *Tetrahedron Lett.*, 27:4051-4054, 1986.
Garegg et al., *Tetrahedron Lett.*, 27:4055-4058, 1986.
Gluck et al., *J. Clin. Invest.*, 90(6):2491-2495, 1992.
Gonda, *Therap. Drug Carrier Sys.*, 6:273-313, 1990.
Goodchild, *Bioconjugate Chem.*, 1:165, 1990.
Gould-Fogerite et al., *AIDS Res. Hum. Retroviruses*, 10(2): S99-103, 1994.
Gupta et al., *Dev. Biol. Stand.*, 92:63-78, 1998.
Hamajima et al., *Clin. Immunol. Immunopathol.*, 88(2):205-210, 1998.
Haq et al., *Science*, 268(5211):714-716, 1995.
Hayashi et al., *Nature*, 410:1099-1103, 2001.
Heil et al., *Eur. J. Immunol.*, 33:2987-2997, 2003.
Hemmi et al., *Nat. Immunol.*, 3:196-200, 2002.
Hemmi et al., *Nature*, 408:740-745, 2000.
Hoet et al., *J. Immunol.*, 163:3304-3312, 1999.
Hone et al., *J. Biotechnol.*, 44(1-3):203-207, 1996.
Hoshino et al., *J. Immunol.*, 162:3749-3752, 1999.
Hu et al., *Clin. Exp. Immunol.*, 113(2):235-243, 1998.
Hunziker et al., *Mod. Synth. Methods*, 7:331-417, 1995.
Ishii et al., *Microbiol. Immunol.*, 41(5):421-425, 1997.
Jabbal-Gill et al., *Vaccine*, 16(20):2039-2046, 1998.
Jiang et al., *J. Virol. Methods*, 78(1-2):81-91, 1999.
Jones et al., *J. Biotechnol.*, 44(1-3):29-36, 1996.
Jurk et al., *Nat. Immunol.*, 3:499, 2002.
Kadowaki et al., *J. Exp. Med.*, 194:863-869, 2001.
Krieg et al., *Nature*, 374:546-549, 1995.
Kuklin et al., *J. Virol.*, 71(4):3138-3145, 1997.
Langer, *Science*, 249:1527-1533, 1990.
Leibl et al., *Vaccine*, 16(4):340-345, 1998.
Lenert et al., *Antisense Nucleic Acid Drug Dev.*, 11:247-256, 2001.
Lenert et al., *Antisense Nucleic Acid Drug Dev.*, 13:143-150, 2003.
Lotz et al., *Mol. Biol. Rep.*, 16:127, 1992.
Lowell et al., *Science*, 240(4853):800-802, 1988.

Lowell et al., *J. Exp. Med.*, 167(2):658-663, 1988.
Lowell et al., *Infect. Immun.*, 64(5):1706-1713, 1996.
Lowell et al., *J. Infect. Dis.*, 175(2):292-301, 1997.
Magnusson et al., *Scand. J. Immunol.*, 54:543-550, 2001.
Malmegrim et al., *Isr. Med. Assoc. J.*, 4:706-712, 2002.
Maloy et al., *Immunology*, 81(4):661-667, 1994.
Mason et al., *Vaccine*, 16(13):1336-1343, 1998.
Medzhitov et al., *Mol. Cell*, 2:253-258, 1998.
Mengiardi et al., *Vaccine*, 13(14):1306-1315, 1995.
Michalek et al., *Curr. Top. Microbiol. Immunol.*, 146:51-58, 1989.
Michalek et al., *Adv. Exp. Med. Biol.*, 327:191-198, 1992.
Mohan et al., *J. Exp. Med.*, 177:1367-1381, 1993.
Moore et al., *Vaccine*, 13(18):1741-1749, 1995.
Morein et al., *Adv. Vet. Med.*, 41:405-413, 1999.
Moren, In: *Aerosols in Medicine. Principles, Diagnosis and Therapy*, Moren et al. (Eds.), Elsevier, Amsterdam, 1985.
Morrow et al., *Curr. Top Microbiol. Immunol.*, 236:255-273, 1999.
Moss et al., *Adv. Exp. Med. Biol.*, 367:7-13, 1996.
Mowat et al., *Immunology*, 80(4):527-534, 1993.
Newkirk et al., *Arthritis Res.*, 3:253-258, 2001.
Nielsen et al., *Bioconjug. Chem.*, 5:3-7, 1994.
Nugent et al., *J. Clin. Pharm. Ther.*, 23(4):257-285, 1998.
Okada et al., *J. Immunol.*, 159(7):3638-3647, 1997.
Ozinsky et al., *Proc. Natl. Acad. Sci. USA*, 97:13766-13771, 2000.
Pasare et al., *Science*, 299:1033-1036, 2003.
PCT Appln. PCT/US03/10406
PCT Appln. WO 00/14217
PCT Appln. WO 02/22125
PCT Appln. WO 95/01363
Poltorak et al., *Science*, 282:2085-2088, 1998.
Pouwels et al., *Int. J. Food Microbiol.*, 41(2):155-167, 1998.
Remington's: *The Science and Practice of Pharmacy*, 19th Ed., Mac Publishing Co., Easton, Pa., 1676-1692, 1995.
Ronnblom et al., *J. Exp. Med.*, 194:F59-63, 2001.
Sasaki et al., *Anticancer Res.*, 18(5D):3907-3915, 1998.
Stirchak et al., *Nucleic Acids Res.*, 17:6129-6141, 1989.
Stover et al., *Nature*, 351(6326):456-460, 1991.
Stunz et al., *Eur. J. Immunol.*, 32:1212-1222, 2002.
Synthesis and Properties & Synthesis and Analytical Techniques, In: *Protocols for Oligonucleotides and Analogs*, Agrawal (Ed.,) Humana Press, Totowa, 1993.
Tacket et al., *Nat. Med.*, 4(5):607-609, 1998.
Takeuchi et al., *Int. Immunol.*, 13:933-940, 2001.
Tarkov et al., *Hely Chim Acta*, 76:481, 1993.
Thomas, In: *Medical Microbiology*, Bailliere Tindall, Great Britain 1983.
Tsai et al., *J. Immunol.*, 150:1137-1145, 1993.
Tsai et al., *Proc. Natl. Acad. Sci. USA*, 89:8864-8868, 1992.
Uhlmann and Peyman, In: *Methods in Molecular Biology*, 20(16):355, Agrawal (Ed.), Humana Press, Totowa, 1993.
Uhlmann et al, *Curr. Opin. Drug Discov. Devel.*, 6:204-217, 2003.
Uhlmann et al., *Chem. Rev.*, 90:543; 544, 1990.
Vallin et al., *J. Immunol.*, 163:6306-6313, 1999.
Vancott et al., *J. Immunol.*, 160(4):2000-2012, 1998.
Vandendriessche et al., *Tetrahedron*, 49:7223, 1993.
ven Venrooij, *J. Clin. Invest.*, 86:2154-2160, 1990.
Wagner et al., *Nat. Biotechnol.*, 14:840-844, 1996.
Wyatt et al., *J. Control Release*, 50(1-3):93-102, 1998.
Yamada et al., *J. Immunol.*, 169:5590-5594, 2002.
Yi et al., *J. Immunol.*, 161:4493-4497, 1998.
Yoshimura et al., *J. Immunol.*, 163:1-5, 1999.
Zeuner et al., *Arthritis Rheum.*, 46:2219-2224, 2002.

What is claimed is:

1. An oligonucleotide of no more than about 50 bases comprising the sequence:

5'-X-Y$_1$Y$_2$-TATCCTGGAGGGGAA-Y$_3$Y$_4$-3'     (SEQ ID NO: 1)

wherein X is T or null, and Y$_1$ and Y$_2$ are independently A, G, C or T, Y$_3$ and Y$_4$ are independently A, G, C, T or null, but excluding TCCTATCCTGGAGGGGAAG (SEQ ID NO:7).

2. The oligonucleotide of claim 1, wherein Y$_1$ and Y$_2$ are the same.

3. The oligonucleotide of claim 1, wherein Y$_1$ and Y$_2$ are different.

4. The oligonucleotide of claim 1, wherein one of Y$_1$ and Y$_2$ are C.

5. The oligonucleotide of claim 1, wherein one of Y$_1$ and Y$_2$ are G.

6. The oligonucleotide of claim 1, wherein one of Y$_1$ and Y$_2$ are A.

7. The oligonucleotide of claim 1, wherein Y$_3$ is G and Y$_4$ is T.

8. The oligonucleotide of claim 1, wherein the oligonucleotide consists of 50 bases.

9. The oligonucleotide of claim 1, wherein the oligonucleotide has a phosphorothioate, phosphoroamidate, phosphodiester or phorphorodithioate backbone.

10. The oligonucleotide of claim 1, wherein said oligonucleotide is dispersed in a pharmaceutically acceptable buffer, diluent or excipient.

11. A method of inhibiting a Toll-like receptor (TLR) signaling comprising contacting a cell expressing a TLR with an oligonucleotide of no more than about 50 bases dispersed in a pharmaceutically acceptable buffer, diluent or excipient, said oligonucleotide comprising the sequence:

5'-X-Y$_1$Y$_2$-TATCCTGGAGGGGAA-Y$_3$Y$_4$-3'     (SEQ ID NO: 1)

wherein X is T or null, and Y$_1$ and Y$_2$ are independently A, G, C or T, Y$_3$ and Y$_4$ are independently A, G, C, T or null, but excluding TCCTATCCTGGAGGGGAAG (SEQ ID NO:7).

12. The method of claim 11, wherein Y$_1$ and Y$_2$ are the same.

13. The method of claim 11, wherein Y$_1$ and Y$_2$ are different.

14. The method of claim 11, wherein one of Y$_1$ and Y$_2$ are C.

15. The method of claim 11, wherein one of Y$_1$ and Y$_2$ are G.

16. The method of claim 11, wherein one of Y$_1$ and Y$_2$ are A.

17. The method of claim 11, wherein Y$_3$ is G and Y$_4$ is T.

18. The method of claim 11, wherein the oligonucleotide consists of 50 bases.

19. The method of claim 11, wherein the oligonucleotide has a phosphorothioate, phosphoroamidate, phosphodiester or phorphorodithioate backbone.

20. The method of claim 11, wherein said oligonucleotide is encapsulated in a lipid delivery vehicle.

21. The method of claim 11, wherein said cell is located in an animal.

22. The method of claim 21, wherein said animal is a human that suffers from or is at risk of an unwanted immune reaction.

23. The method of claim 22, wherein said unwanted immune reaction is an autoimmune reaction, allergic reaction, a detrimental immune response to infection.

24. The method of claim 22, wherein said oligonucleotide is administered orally, intravenously, intra-arterially, subcutaneously, intramuscularly, topically, by inhalation, intranasally, or intraocularly.

25. The method of claim 22, further comprising administering to said human an anti-inflammatory or immunosuppressive agent.

26. The method of claim 25, wherein said cell is a B-cell.

27. The method of claim 25, wherein the TLR is TLR9.

28. The method of claim 23, wherein said infection results in septic shock.

29. A palindromic oligonucleotide of 24 to about 50 bases comprising the sequence:

(SEQ ID NO: 8)
5'-CCTX$_1$X$_2$X$_3$GGGYX$_4$X$_5$Z$_n$X$_6$X$_7$Y'CCCX$_8$X$_9$X$_{10}$AGG-3' wherein X$_1$-X$_5$ are independently A, G, C or T, Y is G or null, Z is a spacer nucleotide segment of length n, wherein n is 0-10, Y' is C when Y is G, and Y' is null where Y is null, X$_6$ is selected so as to base pair with X$_5$, X$_7$ is selected so as to base pair with X$_4$, X$_8$ is selected so as to base pair with X$_3$, X$_9$ is selected so as to base pair with X$_2$, and X$_{10}$ is selected so as to base pair with X$_1$.

30. The oligonucleotide of claim 29, wherein said oligonucleotide is 24-28 residues in length.

31. The oligonucleotide of claim 29, wherein said oligonucleotide is completely palindromic.

32. The oligonucleotide of claim 29, wherein said oligonucleotide comprises a 3' mismatched sequence.

33. The oligonucleotide of claim 32, wherein said mismatched sequence is 1-10 bases in length.

34. The oligonucleotide of claim 29, wherein said oligonucleotide comprises a 5' mismatched sequence.

35. The oligonucleotide of claim 34, wherein said mismatched sequence is 1-10 bases in length.

36. The oligonucleotide of claim 29, having the sequence TATCCTGGAGGGGAATTCCCCTCCAGGATA (SEQ ID NO:9).

37. The oligonucleotide of claim 29, wherein said oligonucleotide is partially palindromic.

* * * * *